US010683498B2

(12) United States Patent
Armstrong et al.

(10) Patent No.: US 10,683,498 B2
(45) Date of Patent: Jun. 16, 2020

(54) METHODS FOR GENERATING CIRCULAR DNA FROM CIRCULAR RNA

(71) Applicant: COFACTOR GENOMICS, INC., St. Louis, MO (US)

(72) Inventors: Jon R Armstrong, St. Louis, MO (US); Jeffrey F Hiken, St. Louis, MO (US)

(73) Assignee: COFACTOR GENOMICS, INC., St. Louis, MO (US)

( * ) Notice: Subject to any disclaimer, the term of this patent is extended or adjusted under 35 U.S.C. 154(b) by 156 days.

(21) Appl. No.: 15/575,681

(22) PCT Filed: May 20, 2016

(86) PCT No.: PCT/US2016/033627
§ 371 (c)(1),
(2) Date: Nov. 20, 2017

(87) PCT Pub. No.: WO2016/187583
PCT Pub. Date: Nov. 24, 2016

(65) Prior Publication Data
US 2018/0148717 A1  May 31, 2018

Related U.S. Application Data

(60) Provisional application No. 62/165,122, filed on May 21, 2015.

(51) Int. Cl.
C12N 15/10 (2006.01)
C12P 19/34 (2006.01)
A41C 3/00 (2006.01)
A41C 3/02 (2006.01)

(52) U.S. Cl.
CPC ........ *C12N 15/1096* (2013.01); *A41C 3/0064* (2013.01); *A41C 3/02* (2013.01); *C12P 19/34* (2013.01)

(58) Field of Classification Search
CPC .......... C12N 15/1096; C12Q 2521/107; C12Q 2521/501; C12Q 2531/125
See application file for complete search history.

(56) References Cited

U.S. PATENT DOCUMENTS

| | | | |
|---|---|---|---|
| 4,661,450 A * | 4/1987 | Kempe | C12N 15/1096 435/320.1 |
| 5,001,050 A | 3/1991 | Blanco et al. | |
| 5,198,543 A | 3/1993 | Blanco et al. | |
| 5,962,272 A | 10/1999 | Chenchik et al. | |
| 6,368,801 B1 | 4/2002 | Faruqi | |
| 6,458,544 B1 | 10/2002 | Miller et al. | |
| 6,620,597 B1 | 9/2003 | Chen et al. | |
| 6,977,153 B2 | 12/2005 | Kumar et al. | |
| 2005/0069938 A1 | 3/2005 | Wang et al. | |
| 2006/0246453 A1 | 11/2006 | Kato et al. | |
| 2013/0157259 A1 | 6/2013 | Choi et al. | |
| 2013/0157269 A1 | 6/2013 | Kim et al. | |
| 2014/0179539 A1 | 6/2014 | Lohman et al. | |
| 2017/0121762 A1* | 5/2017 | Kazakov | C12Q 1/6851 |
| 2017/0362623 A1 | 12/2017 | Armstrong et al. | |
| 2019/0018926 A1 | 1/2019 | Bloom et al. | |

FOREIGN PATENT DOCUMENTS

EP 2570487 A1 3/2013
WO 2004061119 A2 7/2004

OTHER PUBLICATIONS

International Search Report and Written Opinion for PCT/US2015/064141 dated Feb. 25, 2016.
International Search Report and Written Opinion for PCT/US2016/033627 dated Aug. 22, 2016.
Barrett et al., "Circular RNAs: analysis, expression and potential functions", Development, 2016, pp. 1838-1847.
Dean et al., "Rapid Amplification of Plasmid and Phase DNA Using Phy 29 DNA Polymerase and Multiply-Primed Rolling Circle Amplication", Genome Res., Jun. 2001, pp. 1095-1099, vol. 11, Issue 6.
Jeck et al., "Circular RNAs are abundant, conserved, and associated with ALU repeats", RNA, 2013, vol. 19, No. 2, pp. 141-157.
Konishi et al., "Amino Acid Substitutions Away from the RNase H Catalytic Site Increase the Thermal Stability of Moloney Murine Leukemia Virus Reverse Transcriptase Through RNase H Inactivation," Biochem. Biophys Res Commun., Nov. 14, 2014, pp. 269-274, vol. 454, Issue 2.
Aliotta et al.: Thermostable Bst DNA polymerase I lacks a 3'-->5' proofreading exonuclease activity.Genet Anal. (Netherlands) 12: 185-195 (1996).
Bullard et al.: Direct comparison of nick-joining activity of the nucleic acid ligases from bacteriophage T4. Biochem J. 398(1): 135-44 (2006).
Burd et al.: Expression of linear and novel circular forms of an INK4/ARF-associated non-coding RNA correlates with atherosclerosis risk. PLoS Genet. 6(12): p. e1001233 (2010).
Chatterjee et al.: Cloning and overexpression of the gene encoding bacteriophage T5 DNA polymerase. Gene 97: 13-19 (1991).
Goa et al.: CIRI: an efficient and unbiased algorithm for de novo circular RNA identification. Genome Biology 16:4 (2015).
Ho et al.: Characterization of an ATP-dependent DNA ligase encoded by Chlorella virus PBCV-1. J Virol. 71(3):1931-7 (1997).
Jacobsen et al.: The N-terminal amino-acid sequences of DNA polymerase I from *Escherichia coli* and of the large and the small fragments obtained by a limited proteolysis. Eur. J Biochem. 45: 623-627 (1974).

(Continued)

*Primary Examiner* — David C Thomas
(74) *Attorney, Agent, or Firm* — Wilson Sonsini Goodrich & Rosati

(57) ABSTRACT

Provided herein are methods of amplifying nucleic acids. In particular, methods are provided for amplifying circular RNA molecules. In certain embodiments, circular DNA molecules for amplification are generated from circular RNA molecules.

16 Claims, 20 Drawing Sheets

(56) References Cited

OTHER PUBLICATIONS

Jung et al. Bacteriophage PRD1 DNA polymerase: evolution of DNA polymerases. PNAS USA 84:8287-8291 (1987).
Kaboord et al.: Accessory proteins function as matchmakers in the assembly of the T4 DNA polymerase holoenzyme. Curr Biol. 5: 149-157 (1995).
Kong et al.: Characterization of a DNA polymerase from the hyperthermophile archaea Thermococcus litoralis. Vent DNA polymerase, steady state kinetics, thermal stability, processivity, strand displacement, and exonuclease activities. J Biol. Chem. 268: 1965-1975 (1993).
MacNaughton et al.: Rolling Circle Replication of Hepatitis Delta Virus RNA Is Carried Out by Two Different Cellular RNA Polymerases. Journal of Virology. 76(8): 3920-3927 (2002).
Perriman et al.: Circular mRNA can direct translation of extremely long repeating-sequence proteins in vivo. RNA 4(9): 1047-1054 (1998).
Salzman et al.: Cell-type specific features of circular RNA expression. PLoS Genet. 9(9): p. e1003777 (2013).
Salzman et al.: Circular RNAs are the predominant transcript isoform from hundreds of human genes in diverse cell types. PLoS One. 7(2): p. e30733 (2012).
Shore et al.: DNA flexibility studied by covalent closure of short fragments into circles. Proceedings of the National Academy of Sciences of the United States of America.; 78(8): 4833-4837 (1981).
U.S. Appl. No. 15/532,557 Office Action dated Nov. 14, 2018.
Walker et al.: Detection of *Mycobacterium tuberculosis* DNA with thermophilic strand displacement amplification and fluorescence polarization. Clinical Chemistry 42: 1604-1608 (1996).
Wang et al.: Circular RNA Is Expressed across the Eukaryotic Tree of Life. PLoS One. 9(3): p. e90859 (2014).
Zhu et al.: Purification and characterization of PRD1 DNA polymerase. Biochim Biophys Acta. 1219: 267-276 (1994).
European Patent Application No. 16797410.4 Extended Search Report dated Nov. 13, 2018.
European Patent Application No. 16797410.4 Office Action dated Dec. 19, 2019.
International Search Report and Written Opinion of corresponding International Application No. PCT/US2015/064141 dated Feb. 25, 2016, 10 pages.
Lohman et al., Efficient DNA ligation in DNA-RNA hybrid helices by Chlorella virus DNA ligase. Nucleic Acids Res. 42(3): 1831-1844 (2014).
Memczak et al., Circular RNAs are a large class of animal RNAs with regulatory potency. Nature. 495(7441):333-338 (2013).
U.S. Appl. No. 15/532,557 Office Action dated Jun. 28, 2019.
Whiting SH & Champoux JJ, Strand displacement synthesis capability of Moloney murine leukemia virus reverse transcriptase. Journal of Virology. 68(8):4747-4758 (1994).

* cited by examiner

```
<Serial Cloner V2.5>

Restriction analysis of circularizing_GFP_SJ-ori.xdna
[Circular]
Incubated with MfeI + SacI
2 fragments generated.
    1:    640 bp  -  From SacI[738]   To    MfeI[566]
    2:    172 bp  -  From MfeI[566]   To    SacI[738]

<Serial Cloner V2.5>

Restriction analysis of circularizing_GFP_SJ-ori.xdna
[Circular]
Incubated with SacI + NcoI
2 fragments generated.
    1:    566 bp  -  From NcoI[172]   To    SacI[738]
    2:    246 bp  -  From SacI[738]   To    NcoI[172]
```

METHODS FOR GENERATING CIRCULAR DNA FROM CIRCULAR RNA

CROSS-REFERENCE TO RELATED APPLICATIONS

This is a U.S. National Phase application of PCT/US2016/033627, filed on May 20, 2016, which claims the benefit of U.S. Provisional Application No. 62/165,122, filed May 21, 2015, both of which are incorporated herein by reference in theft entirety.

This application is related to PCT App. No. PCT/US2015/064141, filed Dec. 5, 2015, which is incorporated herein by reference in its entirety.

STATEMENT REGARDING FEDERALLY-SPONSORED RESEARCH AND DEVELOPMENT

This invention was made with government support under grant application ID: 1R43DA038993-01 awarded by National Institute on Drug Abuse. The government has certain rights in the invention.

BACKGROUND

Circular RNAs (circRNAs) are a class of RNAs that have been found in multiple organisms and in multiple tissues and cells and have been implicated in various disease processes and cellular pathways. Thus they represent an exciting class of molecules to study in order to better understand biological phenomena. Recent studies suggest that these molecules may bind competitively with microRNAs (miRNAs), play roles in transcriptional regulation, and are important during brain and neural development. It is contemplated that circular RNAs may be of benefit in clinical practice as biomarkers or therapeutic targets. Currently, however, the discovery of novel circular RNAs is hindered because circular RNA molecules are found in much lower amounts than linear RNA molecules. There remains a lack of standardized methods for the enrichment, sequencing, and functional analysis of circular RNA isoforms.

Multiple techniques and strategies have been used to enrich for circular RNA populations from total RNA. Ribosomal RNA depletion and exoribonuclease enzyme digestion are two of the most commonly used strategies. However, to date, no single enrichment protocol has been broadly adopted by researchers studying circular RNA. Circular RNA molecules are present in total RNA pools at 1% of mRNA levels, and their concentration is low compared to other RNA species. Thus, in order to cost effectively and efficiently interrogate the sequence of circular RNA molecules, it is advantageous to increase their concentration versus other RNAs by selectively amplifying circular RNA.

One known method of nucleic acid amplification involves synthesizing first strand cDNA molecules from RNA molecules, circularizing the first strand cDNA molecules, and replicating the circularized first strand cDNA molecules using rolling circle replication (Rolling circle amplification of RNA; U.S. Pat. No. 6,977,153). Another practice includes hybridizing primers to RNA and catalyzing synthesis of cDNA and second-strand DNA resulting in a double stranded DNA copy of a region of the RNA molecule. This double stranded DNA is then fragmented, adapter sequences are ligated to the ends and the primers corresponding to the adapter sequences are used to amplify the DNA copies of the original RNA regions. Another current practice generates cDNA and second strand DNA using a template switching mechanism (Switching Mechanism at 5' End of RNA Template; Methods and compositions for full-length cDNA Cloning using a template-switching oligonucleotide U.S. Pat. No. 5,962,272). A template switching oligonucleotide hybridizes to the CAP site at the 5'-end of the RNA molecule and serves as a short, extended template for CAP-dependent extension of the 3'-end of the ss cDNA that is complementary to the template switching oligonucleotide. The resulting full-length single-stranded cDNA includes the complete 5'-end of the RNA molecule as well as the sequence complementary to the template switching oligonucleotide, which can then serve as a universal priming site in subsequent amplification of the cDNA. Another practice includes hybridizing primers and stopper oligonucleotides to RNA, catalyzing the synthesis of cDNA, until the elongating product nucleic acid reaches the position of an annealed oligonucleotide stopper, whereby the elongation reaction is stopped. The elongated cDNA product is then ligated to the 3' end of the oligonucleotide stopper, thus obtaining an amplified nucleic acid portion (e.g., Nucleic Acid Transcription Method; EP Number 2,570,487).

Since circular RNA molecules share sequence homology to linear RNA, any enrichment technique that relies solely on sequence composition to enrich for circular RNA molecules will also enrich for linear RNA. In contrast, ribosomal transcript reduction strategies are routinely employed to decrease the ratio of ribosomal transcripts to other species, such as circular RNA. (Salzman, J., et al., Circular RNAs are the predominant transcript isoform from hundreds of human genes in diverse cell types. PLoS One, 2012. 7(2): p. e30733; Wang, P. L., et al., Circular RNA Is Expressed across the Eukaryotic Tree of Life. PLoS One, 2014. 9(3): p. e90859; Jeck, W. R., et al., Circular RNAs are abundant, conserved, and associated with ALU repeats. RNA, 2013. 19(2): p. 141-57; Burd, C. E., et al., Expression of linear and novel circular forms of an INK4/ARF-associated non-coding RNA correlates with atherosclerosis risk. PLoS Genet, 2010. 6(12): p. e1001233; Salzman, J., et al., Cell-type specific features of circular RNA expression. PLoS Genet, 2013. 9(9): p. e1003777). However, large amounts of RNA material must be used (20 to 60 µg of total RNA) rendering this technique impractical in most cases (Jeck, W. R., et al., Circular RNAs are abundant, conserved, and associated with ALU repeats. RNA, 2013. 19(2): p. 141-57).

While there are a number of uses for and broadening interest in circular RNAs, these molecules have different properties than circular DNA and therefore there are some applications, treatments, and uses that are better suited to circular DNA molecules as opposed circular RNA molecules. These applications include amplification and subsequent characterization of the molecule. Current methods may generate cDNA fragments from circular RNA, however no current methods generate full cDNA copies of the circular RNA molecule, thus retaining the structure and concomitant sequence readout. This is necessary for studying the function and role of circular RNAs in disease. Thus, it is apparent that a need exists for methods to convert circular RNA molecules into DNA molecules while retaining the original circular structure.

Current methods do not specifically enrich for circular RNA species nor do they retain the circular structure of the RNA templates after cDNA synthesis, because reverse transcriptases will roll around the RNA circle and create multiple and often incomplete copies of the circular RNA template, making it impossible to identify the original circular RNA sequence after intramolecular ligation in downstream analysis. Viroids and viroid-like satellite RNAs from plants, and the human hepatitis delta virus (HDV) RNA replicate their RNA genome through an RNA-based rolling-circle mechanism catalyzed by either the nuclear RNA polymerase II or a nuclear-encoded chloroplastic RNA polymerase (Macnaughton T B, Shi S T, Modahl L E, Lai M M C. Rolling Circle Replication of Hepatitis Delta Virus RNA Is Carried Out by Two Different Cellular RNA Polymerases. Journal of Virology. 2002; 76(8):3920-3927). Neither of these practices, however, generates circular DNA directly from a circular RNA template with the goal to specifically amplify circular RNA species from a complex pool of RNA.

Thus, a need still exists for generating multiple cDNA copies from their circular RNA counterparts in order to better identify rare or previously unknown circular RNAs. In addition, since the circular RNA sequences are copied (amplified) multiple times in the cDNA, significant cost savings may be realized when assaying with next-generation sequencing machines (ex. Illumina, Pacific Biosciences) since fewer reads need to be generated for the same level of sensitivity of circular RNA detection.

SUMMARY

Provided herein are methods for amplifying a nucleic acid. In certain embodiments, a method comprises priming a circular RNA template molecule with one or more DNA primers and extending the primers with a reverse transcriptase to generate a cDNA strand that is a copy of the circular RNA molecule. In certain embodiments, the cDNA strand generated is linear. In certain embodiments, the cDNA strand generated by the reverse transcriptase comprises multiple cDNA copies of the circular RNA molecule. In certain embodiments, the cDNA strand generated by the reverse transcriptase comprises at least 2, 5, 10, 25, 50, 100 or more cDNA copies of the circular RNA molecule. In certain embodiments, the reverse transcriptase extends the cDNA strand beyond the point of origination of primer extension by displacement of the cDNA strand, thereby generating at least a partial additional cDNA copy of the circular RNA molecule on the cDNA strand. In certain embodiments, the reverse transcriptase is an RNA dependent DNA polymerase. In certain embodiments, the RNA dependent DNA polymerase is selected from the group consisting of M-MLV reverse transcriptase from the Moloney murine leukemia virus, HIV-1 reverse transcriptase from human immunodeficiency virus type 1, AMV reverse transcriptase from the avian myeloblastosis virus, and their associated mutants. In certain embodiments, the RNA dependent DNA polymerase is selected from the group consisting of a recombinant of M-MLV reverse transcriptase from the Moloney murine leukemia virus, HIV-1 reverse transcriptase from human immunodeficiency virus type 1, AMV reverse transcriptase from the avian myeloblastosis virus, and their associated mutants, wherein said recombinant exhibits reduced RNase H activity and increased thermostability. In certain embodiments, the circular RNA template molecule is primed by random or non-random priming. In certain embodiments, the circular RNA molecule is primed by random priming using one or more random DNA primers and the one or more random DNA primers is from 6 to 8 bases in length. In certain embodiments, the circular RNA molecule is primed by non-random priming using one or more non-random DNA primers and the one or more non-random DNA primers is at least 8 bases in length. In certain embodiments, the method further comprises amplifying the cDNA strand copy of the circular RNA molecule with a DNA polymerase. In certain embodiments, the DNA polymerase is φ29 DNA polymerase.

Provided herein are also methods of constructing a circular cDNA molecule. The methods comprise ligating with a ligase one or more linear cDNA fragments bound to a circular RNA molecule scaffold, wherein the one or more linear cDNA fragments and the circular RNA molecule scaffold form an RNA-DNA heteroduplex, to convert the one or more linear cDNA fragments into a covalently closed circular cDNA molecule, thereby constructing a circular cDNA molecule. In certain embodiments, the ligase is a ligase that can ligate a 5' DNA end adjacent to a 3' DNA end of the one or more linear DNA fragments bridged by the circular RNA molecule scaffold. In certain embodiments, the ligase is selected from the group consisting of T4 DNA ligase, T4 RNA ligase, and *Paramecium bursaria Chlorella* virus 1 (PBCV-1) DNA Ligase. In certain embodiments, the method further comprises prior to ligation, extending with a reverse transcriptase one or more DNA primers annealed to the circular RNA molecule scaffold to form the one or more linear DNA fragments bound to the circular RNA molecule scaffold. In certain embodiments, the reverse transcriptase is a recombinant of M-MLV reverse transcriptase from the Moloney murine leukemia virus, HIV-1 reverse transcriptase from human immunodeficiency virus type 1, or AMV reverse transcriptase from the avian myeloblastosis virus, and wherein said recombinant exhibits reduced RNase H activity and increased thermostability. In certain embodiments, the method further comprises prior to extending the one or more DNA primers, priming the circular RNA molecule scaffold with the one or more DNA primers. In certain embodiments, the priming of the circular RNA molecule scaffold is by random or non-random priming. In certain embodiments, the circular RNA molecule is primed by random priming using one or more random DNA primers and the one or more random DNA primers is from 6 to 8 bases in length. In certain embodiments, the circular RNA molecule is primed by non-random priming using one or more non-random DNA primers and the one or more non-random DNA primers is at least 8 bases in length. In certain embodiments, the method further comprises prior to ligation, incubating the RNA-DNA heteroduplex with a nuclease that targets single-stranded DNA. In certain embodiments, this nuclease is selected from the group consisting of T5 exonuclease, Mung Bean Nuclease (MBN), *Aspergillus* nuclease S1 (S1 Nuclease), Exonuclease VII (Exo VII), and *Escherichia coli* exonuclease V (RecBCD). In certain embodiments, this nuclease is selected from the group consisting of T5 exonuclease, MBN, and RecBCD. In certain embodiments, this nuclease is T5 exonuclease. In certain embodiments, the method further comprises digesting the RNA portion of the RNA-DNA heteroduplex comprising the circular RNA molecule scaffold and the circular cDNA molecule with an RNase. In certain embodiments, the RNase is RNase H. Certain embodiments comprise following ligation of the one or more linear cDNA fragments bound to the circular RNA molecule scaffold to construct a circular cDNA molecule, incubating a sample comprising the circular cDNA molecule with an exonuclease to digest linear DNA. In certain embodiments, the exonuclease is selected from the group consisting of RecBCD (Exonuclease V), T5 exonuclease, RecJ, Exonuclease T, and Exonuclease VII (Exo VII). In certain embodiments, the exonuclease is T5 exonuclease.

Provided herein are also kits for the use in any method disclosed herein of constructing a circular DNA molecule, the kit comprising a ligase with the ability to ligate adjacent 5' and 3' DNA ends that are bound to RNA in an RNA-DNA heteroduplex, and instructions for use of the kit. In certain embodiments, the ligase selected from the group consisting of T4 DNA ligase, T4 RNA ligase, and *Paramecium bursaria Chlorella* virus 1 (PBCV-1) DNA Ligase. In certain embodiments, the kit comprises a nuclease that targets single-stranded DNA. In certain embodiments, the nuclease is selected from the group consisting of T5 exonuclease, Mung Bean Nuclease (MBN), *Aspergillus* nuclease S1 (S1 Nuclease), Exonuclease VII (Exo VII), and *Escherichia coli* exonuclease V (RecBCD). In certain embodiments, the nuclease is selected from the group consisting of T5 exonuclease, MBN, and RecBCD. In certain embodiments, the kit comprises a reverse transcriptase. In certain embodiments, the reverse transcriptase is selected from the group consisting of recombinant of M-MLV reverse transcriptase from the Moloney murine leukemia virus, HIV-1 reverse transcriptase from human immunodeficiency virus type 1, AMV reverse transcriptase from the avian myeloblastosis virus, and their associated mutants, and wherein said recombinant exhibits reduced RNase H activity and increased thermostability. In certain embodiments, the kit comprises one or more DNA primers. In certain embodiments, at least one DNA primer comprises a modification selected from the group consisting of from 2'fluoro nucleosides, LNA (locked nucleic acid), ZNA (zip nucleic acids), and PNA (Peptide Nucleic Acid). Certain embodiments of a kit comprise an RNAse capable of digesting RNA in an RNA-DNA duplex such as RNAse H. In certain embodiments, the kit comprises a circular RNA control molecule. In certain embodiments, the kit comprises an exonuclease capable of digesting single-stranded or double-stranded DNA. In certain embodiments, the exonuclease is selected from the group consisting of RecBCD (Exonuclease V), T5 exonuclease, RecJ, Exonuclease T, and Exonuclease VII (Exo VII). In certain embodiments, the exonuclease is T5 exonuclease.

BRIEF DESCRIPTION OF THE DRAWINGS/FIGURES

FIG. 1A. FIG. 1A is a schematic of the self-splicing transcript used to generate a circular RNA control. The transcript contains a GFP ORF flanked by group I introns, and undergoes autocatalytic splicing to form a circular GFP ORF. Opposing arrows to the left and right of the 5' splice site indicate the position of PCR primers that flank the GFP ORF and 5' intron boundary, present only in unspliced transcripts.

FIG. 1B. FIG. 1B illustrates a qPCR assay for circular RNA transcripts. The arrows indicate the position of primers flanking the GFP ORF splice junction (SJ) and converge to yield a PCR product only when circularized transcripts are present. On linear transcripts, these primers diverge, yielding no PCR product.

FIG. 1C. FIG. 1C is a picture of a gel showing that self-splicing transcripts were generated by in vitro transcription of Sal I or Hind III linearized plasmid. The self-splicing reaction is about 20% efficient, so IVT products contain a mix of circular GFP ORF molecules and intermediate or unspliced linear transcripts. The products of these IVT reactions were subjected to mock (−) and RNase R digestion (+), and then run on a non-denaturing agarose gel. A band refractory to RNase R digestion (the circularized GFP ORF) is clearly present in the self-splicing IVT reaction products, while control linear RNA is completely degraded (1 Kb Plus ladder, Invitrogen).

FIG. 1D graphically shows the results of: Self-splicing IVT reaction products from Sal I or Hind III linearized plasmid were assayed by SYBR green qPCR using two sets of primers that detect circular GFP ORF (SJ set 1, SJ set 2; arrows in B), or un-spliced linear transcript (5'intron/GFP set 1, 5'intron/GFP set 2; flanking arrows in A). The PCR products detected with the convergent SJ primer sets clearly demonstrate the presence of circular GFP ORF (circular RNA control) that is less susceptible to RNase R degradation than linear unspliced transcripts.

FIG. 2 is a table showing results from TaqMan control assays run against control targets. Empty boxes indicate a negative result where no signal was detected. Boxes populated with a numerical value indicate a positive result for signal detection. The number shown is the mean Ct value.

FIG. 3 shows one embodiment of a molecular workflow for circular RNA amplification and subsequent optional sequencing. In this illustration, random primers are shown mixed with a circular RNA template. Rolling circle amplification (RCA) is shown performed using a reverse transcriptase. Following RCA, a thermostable DNA polymerase can be added to increase the amplification of cDNA from complementary RNA templates. Large amounts of cDNA can be generated during amplification and serve as an input to library production and next generation sequencing.

FIG. 4 shows one embodiment of a molecular workflow for generating a circular cDNA molecule from a circular RNA template molecule and sequencing. RNA template is shown combined with random primers, dNTP mix and reverse transcriptase to generate cDNA from a complementary RNA template. The cDNA reaction products, bound to their complementary RNA templates, are treated with a DNA nuclease in order to digest displaced cDNA flaps and create two adjacent DNA ends that are bridged or "splinted" by a complementary RNA template. In order to ligate the adjacent ends of cDNA products that are splinted by the complementary template RNA, the DNA nuclease reaction products can be mixed with reaction buffer and DNA ligase. The DNA ligase ligates the ends of the adjacent cDNA ends to form covalently closed circular (cccDNA). In order to digest and remove the complementary RNA strands in the RNA:cDNA duplexes (leaving single-stranded linear cDNA and cccDNA) and digest and remove single-stranded linear cDNA (leaving only cccDNA), the ligation products can be treated with Ribonuclease H (RNase H) and an nuclease that only acts as an exonuclease and not as an endonuclease. The resulting products are composed of cccDNA representing the sequences and structure of the original circular RNA templates. These products can then be used in rolling circle amplified (RCA) using, for example, a thermostable DNA polymerase. The RCA products may be suitable for numerous molecular applications.

FIG. 5A is a graphical representation showing total DNA outputs for 10 ng input of linear and circular RNA controls. Amplification reactions were performed with reverse transcriptases RTx (New England Biolabs) and ProtoScript II (PSII; New England Biolabs) alone, combined with *Bacillus stearothermophilus* DNA Polymerase I (BTB3 or BST 3.0; New England Biolabs), or in a two-stage amplification where BTB3 was "spiked" into the reaction following incubation with either RTx or PSII. Higher bars indicate greater amplification. This demonstrates that ProtoScript II and BTB3 exhibit preferential amplification of circular RNA versus linear RNA templates.

FIG. 5B is a graphical representation showing fold amplification of circular RNA (10 ng) for each method shown in FIG. 5A.

FIG. 6A is a graphical representation showing that a two-stage amplification, using ProtoScript II followed by the addition of BTB3 increases amplification of 5 ng circular RNA input with random octamers versus hexamers. Higher bars indicate greater amplification. This illustrates the optimization of circular RNA amplification using increased incubation temperatures and random primer lengths.

Figure 11A:
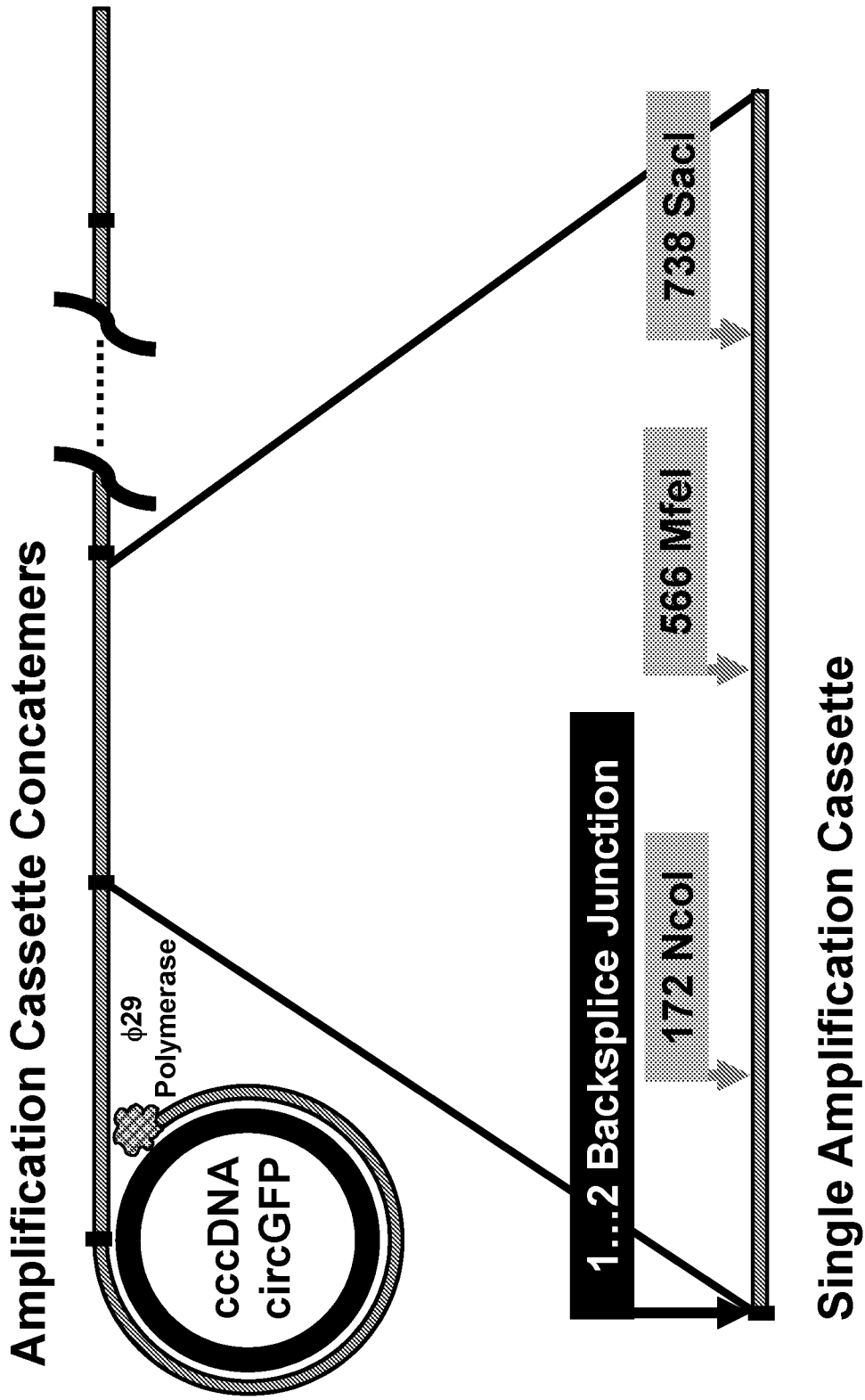

FIG. 11A is a graphic depiction of concatemers and a single cassette generated by rolling circle amplification of covalently closed circular DNA (cccDNA circGFP) generated from the circular GFP control RNA. The relative positions of three different unique restriction enzyme recognition sites are indicated (NcoI, MfeI and SacI) as well as the cccDNA circGFP backsplice junction (1 ... 2 Backsplice Junction).

Figure 11B:
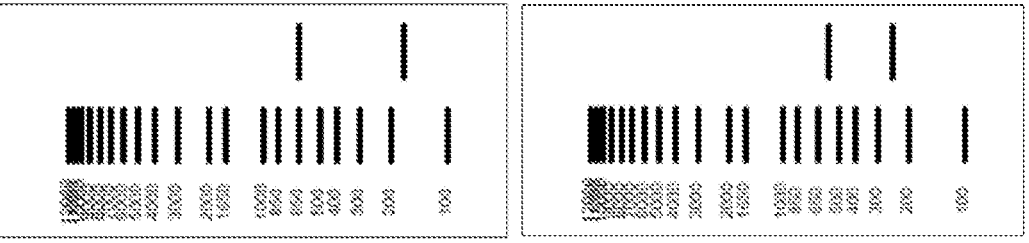

FIG. 11B shows the result of an in silico double restriction enzyme digest of the circular GFP cassette with SacI and MfeI (top), or with SacI and NcoI (bottom).

Figure 11C:
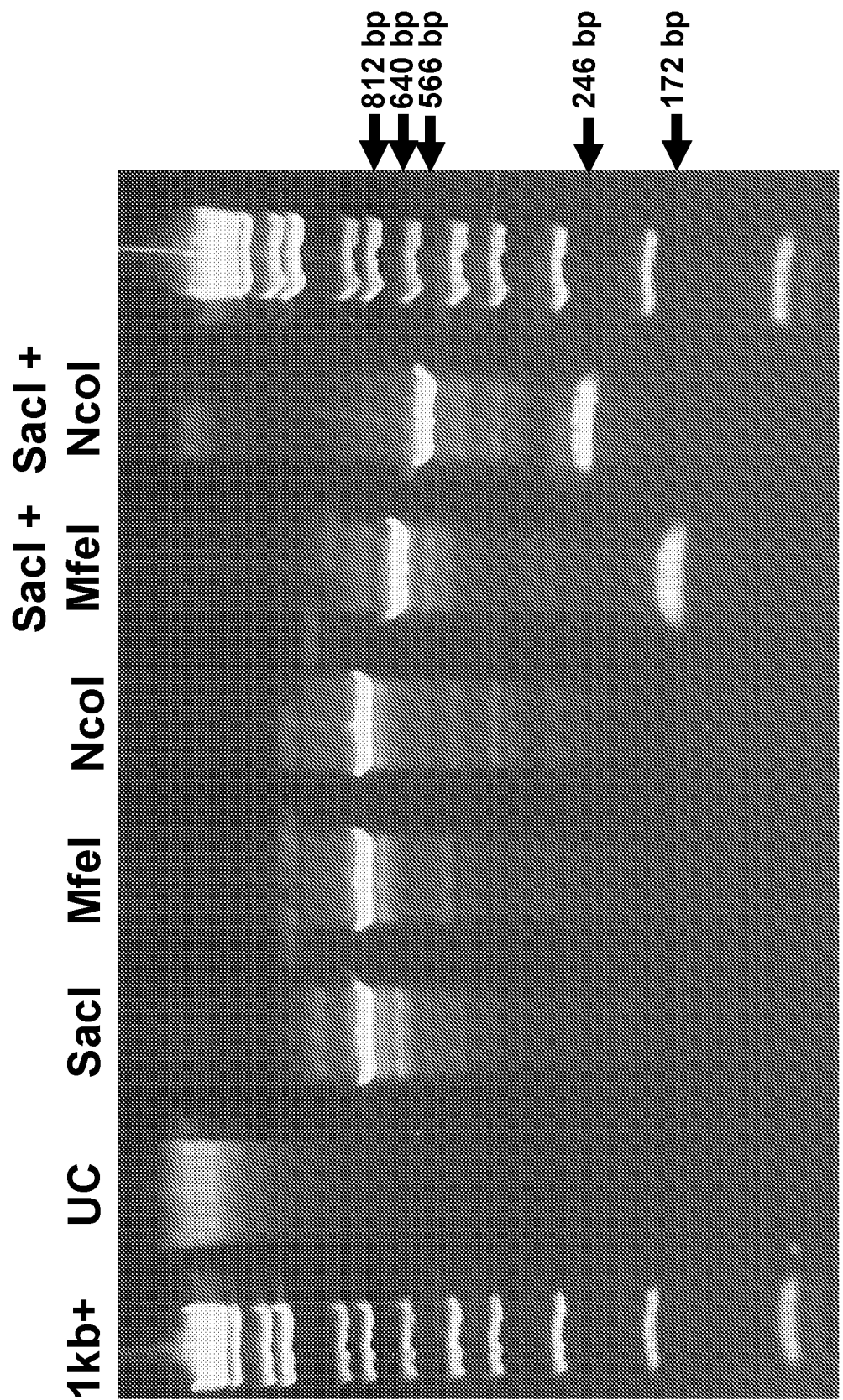

FIG. 11C shows restriction enzyme analysis of φ29 polymerase reaction products derived from amplification of the cccDNA circGFP generated from the circular GFP control RNA.

Figure 12:
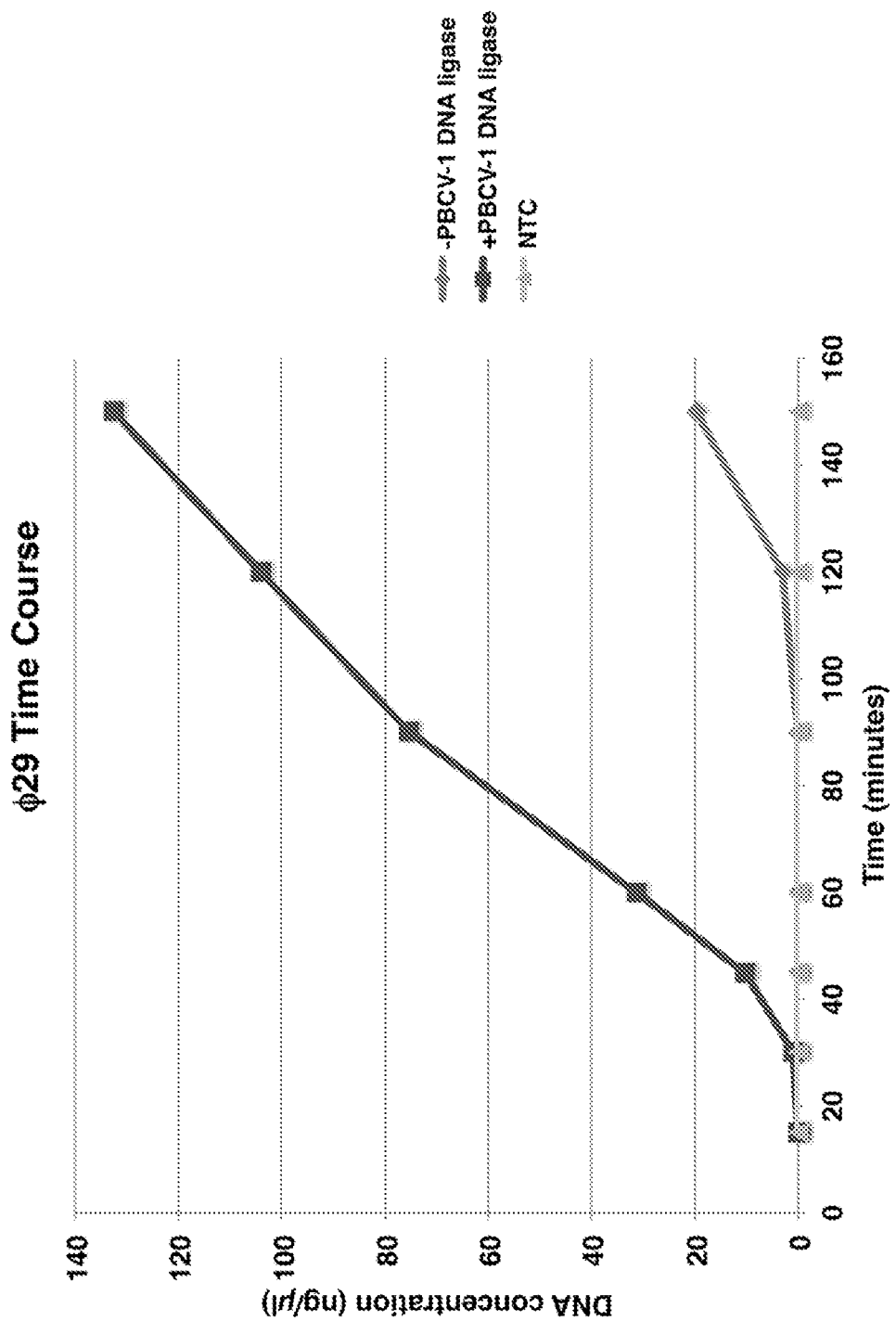

FIG. 12 shows the increase in φ29 amplification products from covalently closed circular DNA molecules.

DETAILED DESCRIPTION

To the extent necessary to provide descriptive support, the subject matter and/or text of the appended claims is incorporated herein by reference in their entirety. It will be understood by all readers of this written description that the exemplary embodiments described and claimed herein may be suitably practiced in the absence of any recited feature, element or step that is, or is not, specifically disclosed herein.

Definitions

It is to be noted that the term "a" or "an" entity refers to one or more of that entity; for example, "a ligase," is understood to represent one or more ligases. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

All methods described herein can be performed in any suitable order unless otherwise indicated herein. No language or terminology in this specification should be construed as indicating any non-claimed element as essential or critical.

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Concentrations, amounts, and other numerical data may be presented here in a range format (e.g., from 5% and 20%). It is to be understood that such range format is used merely for convenience and brevity and should be interpreted flexibly to include not only the numerical values explicitly recited as the limits of the range, but also to include all the individual numerical values or subranges encompassed within that range, as if each numerical value and subrange is explicitly recited. For example, a range of from 5% to 20% should be interpreted to include numerical values such as, but not limited to, 5%, 5.5%, 9.7%, 10.3%, 15%, etc., and subranges such as, but not limited to, 5% to 10%, 10% to 15%, 8.9% to 18.9%, etc.

Units, prefixes, and symbols are denoted in their Systeme International de Unites (SI) accepted form. Numeric ranges are inclusive of the numbers defining the range.

The headings provided herein are not limitations of the various aspects or aspects of the disclosure, which can be had by reference to the specification as a whole.

As used herein, the terms "scaffold" (e.g., circular RNA scaffold) and "template" (e.g., circular RNA template) are used interchangeably unless otherwise specified. An RNA template/scaffold is an RNA molecule to be copied thus serving as the sequence template to generate a cDNA copy and also the physical circular scaffold to which a cDNA strand can be bound.

A circular RNA molecule to be copied can be a naturally occurring circular RNA molecule or a circular RNA molecule that has resulted from some prior process or upstream manipulation. A circular RNA molecule can be comprised of as few bases as physically necessary to create a closed circular RNA or may be many thousand bases in length, as long as it is circular and comprises and/or consists of RNA (Shore D, Langowski J, Baldwin R L. DNA flexibility studied by covalent closure of short fragments into circles. *Proceedings of the National Academy of Sciences of the United States of America.* 1981; 78(8):4833-4837.).

As used herein, unless otherwise specified, a single-stranded DNA molecule is one that is not bound to a complementary DNA or RNA strand.

A ligase is an enzyme used to covalently link or ligate (ligating, ligation, etc.) fragments of DNA or RNA molecules together. DNA ligation catalyzes the formation of a phosphodiester bond between the 3' hydroxyl and 5' phosphate of adjacent DNA residues. In the disclosed methods, this reaction can be used to catalyze the ligation of adjacent, single-stranded DNA (ssDNA) bridged by a complementary RNA strand. RNA ligation catalyzes the ligation of a 5' phosphoryl-terminated nucleic acid donor to a 3' hydroxyl-terminated nucleic acid acceptor through the formation of a 3'→5' phosphodiester bond. It is understood that certain ligases can act upon either DNA or RNA.

The concept of complementary nucleic acid base pairing is well known in the art. Consistent with this understanding, as used herein, "annealing" means for complementary sequences of single-stranded DNA or RNA to pair by hydrogen bonds to form a double-stranded polynucleotide. Where one strand is RNA and the other is DNA, the double-stranded polynucleotide can be referred to as an RNA-DNA heteroduplex molecule. As used herein, the "annealing" is generally used to describe the binding of a primer or probe to a template sequence.

Overview

Unless otherwise specified, the embodiments disclosed in this section can be used in any of the methods described in this disclosure.

Provided herein are methods of amplifying nucleic acid molecules via rolling circle amplification. In certain embodiments, rolling circle cDNA amplification products are generated directly from a circular RNA molecule as a substrate using a reverse transcriptase with strand displacement ability. This allows one to preferentially amplify circular RNA molecules versus linear RNA molecules. In addition, since the circular RNA sequences can be copied (amplified) multiple times in the resulting cDNA strand, significant cost savings may be realized when assaying with next-generation sequencing machines (ex. Illumin, Pacific Biosciences) since fewer reads need to be generated for the same level of sensitivity of circular RNA detection.

Circular RNA molecules can be contained in samples comprising RNA, i.e., an RNA sample. RNA samples can be obtained from a biological source. Illustrative biological source samples include, but are not limited to, RNA isolated from: blood; extracellular vesicles, cultured cells; formalin-fixed paraffin-embedded (FFPE) tissue, plants, tissue, yeast, bacteria, and viral RNA from liquid and cell-free samples. RNA samples can also come from non-biological sources such as synthetic reactions.

In certain embodiments, the amplification is of a circular RNA (circRNA) molecule using a reverse transcriptase. A reverse transcriptase (RT) is an enzyme capable of generating a complementary DNA strand (cDNA) from an RNA template. Reverse transcriptases can synthesize a cDNA strand initiating from a primer using either RNA (cDNA synthesis) or single-stranded DNA as a template. Reverse transcriptases synthesize DNA from 3' end of the primer in the 5' to 3' direction (with respect to the template strand). Other names for reverse transcriptases include: DNA nucleotidyltransferase (RNA-directed); revertase; RNA-dependent deoxyribonucleate nucleotidyltransferase; RNA revertase; RNA-dependent DNA polymerase; and RNA-instructed DNA polymerase. In certain embodiments, the reverse transcriptase is an RNA dependent DNA polymerase. In certain embodiments, the reverse transcriptase is a recombinant enzyme that exhibits reduced RNase H activity and increased thermostability in comparison to corresponding non-recombinant enzymes. Examples of recombinant reverse transcriptases include mutants and/or recombinants of AMV Reverse Transcriptase and M-MLV (aka M-MuLV) Reverse Transcriptase, e.g., ProtoScript II or NxGen® M-MuLV Reverse Transcriptase.

In certain embodiments, the circular RNA template has a known sequence and in certain embodiments, methods disclosed herein can create cDNA copies from a pool of circular RNA molecules with unknown sequences. Circular RNA molecules can be primed, such as for amplification, by one or more oligonucleotide primers. In certain embodiments, the oligonucleotide primer is a nucleic acid such as a DNA molecule or an RNA molecule. In certain embodiments, oligonucleotide primers can comprise modifications. For example, potential modifications include 2'fluoro nucleosides, LNA (locked nucleic acid), ZNA (zip nucleic acids), and PNA (Peptide Nucleic Acid).

An oligonucleotide primer can be at least about 6 bases in length. A primer can be at least about 8 bases in length. A primer can be about 6, 7, or 8 bases in length. A primer can be from about 6 bases up to about 10, 20, 30, 40, 50, or 100 bases in length. Priming of a circular RNA molecule in any of the methods described herein can be done with one or more sequence and/or gene specific primers or with random primers.

Random primers are oligonucleotide sequences of n bases that can be synthesized entirely randomly and can consist of every possible combination of bases forming a numerous range of sequences that have the potential to anneal at many random points on a DNA or RNA sequence and act as a primer to commence DNA or RNA synthesis.

A sequence or gene specific primer can be used for copying and amplification transcripts of a known sequence or gene, for example when the sequence of a gene is known or predicted. Sequence or gene specific primers can also be employed as a mixture of primers specific to a single gene or to multiple genes. Sequence specific or gene specific priming or primers is also referred to herein as "non-random" priming or primers.

Degenerate primers are a mix of oligonucleotide sequences in which some positions contain a number of possible bases, giving a population of primers with similar sequences that cover multiple or all possible nucleotide combinations for a given sequence. They may be advantageous if the same gene is to be amplified from different organisms, as the genes themselves are often similar but not identical. Another use for degenerate primers is when primer design is determined from protein sequence. Because of the degenerate nature of the amino acid code, i.e., several different codons can code for one amino acid, it is often difficult to deduce which codon is used in a particular case. For example, a primer sequence corresponding to the amino acid isoleucine might be "ATV", where A stands for adenine, T for thymine, and V for adenine, cytosine, or guanine according to the genetic code for each codon, using the IUPAC symbols for degenerate bases. For the purposes of this disclosure, unless specified otherwise, degenerate primers are a type of sequence or gene specific primer, also referred to as a non-random primer. In certain embodiments, primers can be either enriched or reduced for certain sequence motifs.

When a circular RNA molecule has been primed, extension of the one or more primers with a reverse transcriptase generates a DNA copy (cDNA) of the circular RNA molecule. In certain embodiments, the reverse transcriptase continues catalyzing cDNA past the original point of origination by displacing the origination point of the cDNA strand. In certain embodiments, the reverse transcriptase can continue to displace the previously generated cDNA strand and continue to catalyze cDNA around the circular RNA, thus generating at least a partial additional DNA copy (cDNA) or multiple DNA copies (cDNAs) of the original circular RNA sequence. These copies can be used themselves as templates for amplification and downstream applications such as real-time PCR, next-generation sequencing, direct gene amplification, library construction, subtractive hybridization, probes for arrays, etc.

In certain embodiments, a circular DNA molecule is created from a circular RNA molecule. One or more primers and a reverse transcriptase (e.g., an RNA-dependent DNA polymerase) can be used to generate a DNA copy (cDNA), with adjacent ends, of the circular RNA template molecule. A ligase, such as a T4 Ligase or *Paramecium bursaria Chlorella* virus DNA Ligase (PBCV-1 DNA ligase (New England Biolabs)), can catalyze the ligation of adjacent cDNA ends bridged by a circular RNA template molecule, for example, while the cDNA copy is still associated with the corresponding circular RNA molecule (DNA-RNA heteroduplex) (Ho, C K. J Virol. 1997 March; 71(3):1931-7; Bullard, D R. Biochem J. 2006 Aug. 15; 398(1):135-44.) Once the DNA ends are ligated, a covalently closed circular cDNA (cccDNA) molecule is created. These circular cDNA molecules can be used, for example, for rolling circle amplification using a DNA polymerase such as φ29 or Bst Polymerase. Rolling circle replication of the circularized first strand cDNA molecules results in long DNA strands containing tandem repeats of the cDNA sequence, thus amplifying multiple cassette copies of the original circular RNA sequence.

RNA Rolling Circle Amplification

In certain embodiments, an RNA template is combined with one or more primers and a mix of dNTPs for extending the primers. In certain embodiments, a mix of dNTPs is a deoxynucleotide (dNTP) solution comprising dATP, dCTP, dGTP and dTTP. In certain embodiments, the solution comprises and equal mix of dATP, dCTP, dGTP and dTTP. In certain embodiments, the dNPTs can be labeled and/or modified with a fluorophore or other modification. In certain embodiments, an appropriate buffer can also be included. The one or more primers can be a single gene specific primer or multiple gene specific primers. The primers can also be random primer sequences. The length of the primer sequence can be from about 6 to about 100 bases or more. For example, the primer may be a hexamer (i.e., 6 nucleotide bases), a heptamer (i.e., 7 nucleotide bases), or an octamer (i.e., 8 nucleotide bases).

To prime a circular RNA molecule for primer extension (e.g., allow the primers to anneal to the RNA molecules through complementary base pairing), a mixture comprising RNA template and primers is incubated at from about 50° C. to about 90° C., or from about 55° C. to about 75° C., or from about 60° C. to about 70° C., or from about 64° C. to about 66° C., or about 65° C., for a time from about 10 seconds and 30 minutes, from about 60 second to about 10 minutes. In certain embodiments, the mixture is incubated at this step for a time of from about 3 minutes to about 7 minutes, or about 4 minutes to about 6 minutes, or about 5 minutes. The temperature is then reduced to promote the primers annealing to the template molecule. In certain embodiments, the temperate is reduced to about 0° C. to about 25° C. For shorter primers, e.g., random hexamers or octamers, this temperature may be higher than for longer gene specific primers for which a lower temperature, e.g., around 0° C., may be preferred. In certain embodiments, the temperature is reduced to about room temperature or to about 25° C. In certain embodiments, the temperature is reduced to about 0° C. to about 4° C., such as by placing on ice. In certain embodiments, the mixture is chilled rapidly to about 0° C. to about 4° C.

After priming, a reverse transcriptase is added. Representative examples of reverse transcriptases are Protoscript II [New England Biolabs] and PrimeScript [Clontech]. Other examples include M-MLV reverse transcriptase from the Moloney murine leukemia virus, HIV-1 reverse transcriptase from human immunodeficiency virus type 1, AMV reverse transcriptase from the avian myeloblastosis virus, and their associated mutants and/or recombinants. A suitable reaction buffer can also be added. In certain embodiments, the reaction mixture is incubated at a temperature of from about 37° C. to about 65° C., or about 40° C. to about 50° C., or about 42° C. to about 48° C., or about 43° C. to about 47° C., or about 45° C., for a time of from about 30 minutes to about 120 minutes, or about 40 minute to about 60 minutes, or about 45 minutes to about 55 minutes, or about 50 minutes.

In certain embodiments, a "pre-incubation" is done prior to the above reaction mixture incubation. The pre-incubation can be done at a temperature of from about 20° C. to about 30° C. for about 2 minutes to about 60 minutes. In certain embodiments, the pre-incubation is done at a temperature of from about 22° C. to about 28° C. for about 2 minutes to about 60 minute or for about 5 minutes to about 15 minutes. In certain embodiments, the pre-incubation is done at a temperature of from about 23° C. to about 27° C. for about 2 minutes to about 60 minute or for about 5 minutes to about 15 minutes or for about 8 minutes to about 12 minutes. In certain embodiments, the pre-incubation is done at a temperature of about 25° C. for about 10 minutes. In certain embodiments, the pre-incubation is done when using random primers.

Optionally, a DNA polymerase, such as BST polymerase or phi29 (φ29) polymerase, can be added to increase the amount of amplification products. In certain embodiments, the incubation time of the DNA polymerase is up to about 30 minutes to about 24 hours, or about 60 minutes to about 10 hours, or about 120 minute to about 6 hours, or about 200 minutes to about 5 hours, or about 240 minutes, at a temperature of from about 20° C. to about 37° C., or about 25° C. to about 35° C., or about 28° C. to about 32° C., or about 30° C.

DNA polymerases are enzymes that are capable of creating DNA molecules by assembling nucleotides. DNA polymerases catalyze the step-by-step addition of deoxyribonucleotide units to a DNA chain by adding new nucleotides matched to the template strand one at a time via the creation of phosphodiester bonds. When creating DNA, DNA polymerases can add free nucleotides only to the 3' end of the newly forming strand. No known DNA polymerase is able to begin a new chain (de novo); it can only add a nucleotide onto a pre-existing 3'-OH group, and therefore needs a primer at which it can add the first nucleotide.

Useful strand displacement DNA polymerases include *Bacillus subtilis* phage φ29 (φ29) DNA polymerase (U.S. Pat. Nos. 5,198,543 and 5,001,050 to Blanco et al.), Bst large fragment DNA polymerase (Exo(–) Bst; Aliotta et al., *Genet. Anal.* (*Netherlands*) 12:185-195 (1996)) and exo(–) Bca DNA polymerase (Walker and Linn, *Clinical Chemistry* 42:1604-1608 (1996)). Other useful polymerases include phage φPRD1 DNA polymerase (Jung et al., *Proc. Natl. Acad. Sci. USA* 84:8287 (1987)), exo(–)VENT® DNA polymerase (Kong et al., *J. Biol. Chem.* 268:1965-1975 (1993)), Klenow fragment of DNA polymerase I (Jacobsen et al., *Eur. J. Biochem.* 45:623-627 (1974)), T5 DNA polymerase (Chatterjee et al., *Gene* 97:13-19 (1991)), Sequenase (U.S. Biochemicals), PRD1 DNA polymerase (Zhu and Ito, *Biochim. Biophys. Acta.* 1219:267-276 (1994)), and T4 DNA polymerase holoenzyme (Kaboord and Benkovic, *Curr. Biol.* 5:149-157 (1995)). In certain embodiments, the polymerase lacks 5'→3' exonuclease activity.

Circular DNA from Circular RNA

Provided herein are methods for replicating the information stored in the nucleotide sequence of a circular RNA molecule by converting the RNA molecule into a circular DNA molecule. Such conversion can be utilized by downstream applications, characterizations, and serves goals that are better suited to having the molecule represented as DNA as opposed to RNA.

By generating and amplifying circular DNA molecules from their circular RNA counterparts, rare or previously unknown circular RNAs may be identified. Provided herein are methods allowing for at least 10 fold greater sensitivity of detection, which it is estimated correlates to a nearly a 10-fold cost savings on sequencing reagents compared to current methods.

Creating an accurate cDNA copy of a circular RNA molecule before rolling circle amplification of the cDNA copy can be crucial in order to accurately identify the original circular RNA sequence in downstream analysis, for example, using next generation sequencing or similar methods. In certain of the methods provided herein, circular RNA molecules are specifically targeted for circular DNA creation. Currently, circular cDNA is synthesized from linear RNA templates first to create a linear cDNA molecule from the linear RNA template and then circularizing the cDNA using intramolecular ligation of the 5' and 3' ends. This method will not work, however, when starting from circular RNA template because reverse transcriptases will continue to extend the cDNA strand around the circular RNA template and create linear cDNA molecules that contain multiple and often incomplete copies of the original circular RNA. Thus, these copies may not accurately represent the circular RNA sequence after intramolecular ligation.

Methods disclosed herein employ cDNA synthesis, for example using a reverse transcriptase, but while the cDNA remains bound to the RNA template as a DNA-RNA heteroduplex, a ligation reaction is performed using an enzyme that specifically catalyzes the ligation of adjacent, single-stranded DNA bridged by a complementary RNA strand. This ligation forms a circular cDNA molecule that is a copy of the circular RNA molecule, as opposed to a linear cDNA copy of the circular RNA molecule. In certain embodiments, these ends can have specific properties, such as modification, phosphorylation, and/or a terminal hydroxyl group. The purpose is that circular cDNA that matches a circular RNA template molecule is preferentially created.

The disclosed methods can further comprise additional enzymatic step(s) to create adjacent cDNA ends on the circular RNA template. This can increase the efficiency and sensitivity of the enrichment methods.

It has been discovered that when performing the methods on a mixture of both circular RNA and linear RNA molecules, linear cDNA will also be created from the linear RNA species. Linear cDNA molecules, however, can be removed if desired, such as by using nucleases. For example, prior to rolling circle amplification of the circular DNA molecules.

In addition, in certain embodiments, an RNase such as RNase H can be used to digest back RNA, including linear RNA molecules and the circular RNA scaffold.

In certain embodiments, the reverse transcriptase creates approximately one (1) cDNA copy of the circular RNA template. This can be achieved by optimizing the processivity of the reverse transcription reaction conditions, such as by optimizing the temperature.

In certain embodiments, the temperature is in a range that optimizes the use of random DNA primer sequences to enrich circular RNAs with unknown sequences from a pool of RNA molecules.

In certain embodiments, a method further includes the use of DNA nucleases, such as T5 Exonuclease, Mung Bean Nuclease (MBN), *Aspergillus* nuclease S1 (S1 Nuclease), Exonuclease VII (Exo VII), or *Escherichia coli* exonuclease V (RecBCD), to digest back cDNA products that were displaced during the reverse transcriptase reaction and are not bound to the RNA template molecule to create adjacent cDNA ends. In certain embodiments, the nuclease is MBN or RecBCD. The need to digest back cDNA products that were displaced during the reverse transcriptase reaction formed from the circular RNA template molecule may be dependent on the displacement ability of the reverse transcriptase that is used.

In certain embodiments, the nuclease is T5 Exonuclease. T5 Exonuclease can degrade circular dsDNA from gaps or nicks ("gap endonuclease activity) (Sayers and Eckstein, Nucl. Acids Res. (1991) 19 (15):4127-4132). However, T5 does not degrade supercoiled DNA (i.e., closed circular dsDNA; Sayers and Eckstein, JBC 265: pp. 18311-18317). One common use of T5 Exonuclease is to remove nicked dsDNA plasmid from supercoiled plasmid (closed circular dsDNA), which would be expected to degrade nicked circular dsDNA. Further, it has been shown that T5 Exonuclease removes the flap from DNA:DNA hybrids and also removes one additional base in from the flap, creating a gap between the two DNA ends. Thus two DNA strands cannot be ligated together because there is a gap and not a nick. It has been discovered, however, that T5 Exonuclease removes the flap, but does not remove the extra base inward when used on a DNA:RNA hybrid. (See Examples below). This activity unexpectedly allows the creation of ligatable adjacent ends of DNA following flap removal on a DNA:RNA hybrid.

In certain embodiments, a DNA ligase, such as a PBCV-1 DNA Ligase, T4 DNA ligase, or T4 RNA ligase (U.S. Pat. No. 6,368,801; US Pub. No. 2014/0179539), is used to ligate adjacent ends of a cDNA molecule bound to a circular RNA scaffold to create a covalently closed circular cDNA molecule.

In certain embodiments, an RNA template is combined with one or more primers. The primers can be non-random or random primers. To the RNA template and primers is added dNTPs, such as supplied in an appropriate ratio for DNA strand extension. In certain embodiments, a mix of dNTPs is a deoxynucleotide (dNTP) solution comprising dATP, dCTP, dGTP and dTTP. In certain embodiments, the solution comprises and equal mix of dATP, dCTP, dGTP and dTTP. In certain embodiments, the dNPTs can be labeled and/or modified with a fluorophore or other modification. In certain embodiments an appropriate buffer is also included. In certain embodiments, the RNA template is primed with the primers by incubating a mixture comprising RNA and DNA primers at a temperature of from about 50° C. to about 90° C., or from about 55° C. to about 75° C., or from about 60° C. to about 70° C., or from about 64° C. to about 66° C., or about 65° C., for a time from about 10 seconds and 30 minutes, from about 60 second to about 10 minutes. In certain embodiments, the mixture is incubated at this step for a time of from about 3 minutes to about 7 minutes, or about 4 minutes to about 6 minutes, or about 5 minutes. The temperature is then reduced to promote the primers annealing to the template molecule. In certain embodiments, the temperature is reduced to about 0° C. to about 25° C. For shorter primers, e.g., random hexamers or octamers, this temperature may be higher than for longer gene specific primers for which a lower temperature, e.g., around 0° C., may be preferred. In certain embodiments, the temperature is reduced to about room temperature or to about 25° C. In certain embodiments, the temperature is reduced to about 0° C. to about 4° C. In certain embodiments, the mixture is cooled rapidly, such as placing it on ice.

Next, a reverse transcriptase is added (e.g., M-MLV reverse transcriptase from the Moloney murine leukemia virus, HIV-1 reverse transcriptase from human immunodeficiency virus type 1, AMV reverse transcriptase from the avian myeloblastosis virus, and their associated mutants and/or recombinants; Protoscript II [New England Biolabs], PrimeScript [Clontech]) to form a reaction mixture and the reaction mixture is incubated at a temperature at which the reverse transcriptase is enzymatically active. In certain embodiments, the reaction mixture is incubated at a temperature of from about 20° C. to about 65° C. for about 5 minutes to about 120 or about 145 minutes. In certain embodiments, the reaction mixture is incubated at a temperature of about 37° C. to about 45° C. for about 40 minutes to about 60 minutes. In certain embodiments, the reaction mixture is incubated at a temperature of about 40° C. to about 44° C. for about 40 minutes to about 60 minutes. In certain embodiments, the reaction mixture is incubated at a temperature of about 41° C. to about 43° C., or about 42° C., for about 40 minutes to about 60 minutes or for about 45 minutes to about 55 minutes, or about 50 minutes. In certain embodiments, an appropriate reaction buffer is included in the reaction mixture.

In certain embodiments, a "pre-incubation" is done prior to the above reaction mixture incubation. The pre-incubation can be done at a temperature of from about 20° C. to about 30° C. for about 2 minutes to about 60 minutes. In certain embodiments, the pre-incubation is done at a temperature of from about 22° C. to about 28° C. for about 2 minutes to about 60 minute or for about 5 minutes to about 15 minutes. In certain embodiments, the pre-incubation is done at a temperature of from about 23° C. to about 27° C. for about 2 minutes to about 60 minute or for about 5 minutes to about 15 minutes or for about 8 minutes to about 12 minutes. In certain embodiments, the pre-incubation is done at a temperature of about 25° C. for about 10 minutes. In certain embodiments, the pre-incubation is done when using random primers. In certain embodiments, the reaction can be cleaned up, for example using a solid phase reversible immobilization (SPRI) bead cleanup and eluted in an appropriate buffer solution or water. (Other methods of reaction cleanup at this or other stages include ethanol precipitation or column based cleanup).

The cDNA reaction products, including those bound to their complementary circular RNA templates, can mixed with a DNA nuclease capable of digesting single-stranded DNA (e.g., Mung Bean Nuclease or T5 Exonuclease) to digest displaced cDNA flaps and create two adjacent DNA ends bridged by a complementary circular RNA template. This nuclease can have endonuclease activity, exonuclease activity, or both, so long as it targets single-stranded DNA. In certain embodiments, a nuclease buffer is included. (Optionally, the mixture is incubated at a temperature sufficient to lessen or remove secondary structure in the strand displacement flaps (e.g., at about 70° C.). This can be followed by quenching on ice (or equivalent cooling) for at least about 2 minutes. The nuclease mixture is then incubated.) The nuclease mixture is incubated at a temperature at which the nuclease is enzymatically active. In certain embodiments, for example, at a temperature of about 25° C. to about 42° C., or about 25° C. to about 37° C., or about 28° C. to about 32° C., or about 30° C., or about 30° C. to about 42° C., or about 30° C. to about 40° C., or about 35° C. to about 42° C., or about 35° C. to about 40° C., or about 35° C. to about 39° C., or about 36° C. to about 42° C., or about 36° C. to about 40° C., or about 36° C. to about 39° C., or about 36° C. to about 38° C., or about 37° C. In certain embodiments, the nuclease mixture is incubated for about 10 or about 15 minutes to about 120 minutes, or about 15 minutes to about 45 minutes, or about 25 minutes to about 35 minutes, or about 30 minutes, or about 30 minutes to about 120 minutes, or about 45 minutes to about 120 minutes, or about 60 minutes to about 120 minutes, or about 30 minutes to about 90 minutes, or about 45 minutes to about 90 minutes, or about 60 minutes to about 90 minutes, or about 10 minutes to about 60 minutes, or about 20 minutes to about 60 minutes, or about 30 minutes to about 60 minutes, or about 45 minutes to about 60 minutes, or about 10 minutes to about 75 minutes, or about 20 minutes to about 75 minutes, or about 30 minutes to about 75 minutes, or about 45 minutes to about 75 minutes, or about 50 minutes to about 70 minutes, or about 55 minutes to about 65 minutes, or about 60 minutes. The reaction mixture can be cleaned up with a second SPRI bead cleanup and eluted in an appropriate buffer solution or water.

The adjacent ends of cDNA products, which are bridged by the complementary circular RNA template, can then be ligated with a DNA ligase to form covalently closed circular DNA molecules (cccDNA). In certain embodiments, this ligation is performed at about 16° C. to about 37° C. for about 5 minutes to about 120 minutes. In certain embodiments, this ligation is performed at about 20° C. to about 30° C. for about 5 minutes to about 120 minutes, or for about 15 minutes to about 45 minutes, or for about 25 minutes to about 35 minutes, or for about 30 minutes, or about 30 minutes to about 120 minutes, or about 45 minutes to about 120 minutes, or about 60 minutes to about 120 minutes, or about 30 minutes to about 90 minutes, or about 45 minutes to about 90 minutes, or about 60 minutes to about 90 minutes, or about 10 minutes to about 60 minutes, or about 20 minutes to about 60 minutes, or about 30 minutes to about 60 minutes, or about 45 minutes to about 60 minutes, or about 10 minutes to about 75 minutes, or about 20 minutes to about 75 minutes, or about 30 minutes to about 75 minutes, or about 45 minutes to about 75 minutes, or about 50 minutes to about 70 minutes, or about 55 minutes to about 65 minutes, or about 60 minutes. In certain embodiments, this ligation is performed at a temperature of about 23° C. to about 33° C., or about 23° C. to about 27° C., or at about 25° C., or about 25° C. to about 33° C., or about 27° C. to about 33° C., or about 28° C. to about 32° C., or about 29° C. to about 31° C., or about 30° C., for about 5 minutes to about 120 minutes, or for about 15 minutes to about 45 minutes, or for about 25 minutes to about 35 minutes, or for about 30 minutes, or about 30 minutes to about 120 minutes, or about 45 minutes to about 120 minutes, or about 60 minutes to about 120 minutes, or about 30 minutes to about 90 minutes, or about 45 minutes to about 90 minutes, or about 60 minutes to about 90 minutes, or about 10 minutes to about 60 minutes, or about 20 minutes to about 60 minutes, or about 30 minutes to about 60 minutes, or about 45 minutes to about 60 minutes, or about 10 minutes to about 75 minutes, or about 20 minutes to about 75 minutes, or about 30 minutes to about 75 minutes, or about 45 minutes to about 75 minutes, or about 50 minutes to about 70 minutes, or about 55 minutes to about 65 minutes, or about 60 minutes. In certain embodiments, the ligase mixture includes a reaction buffer. In certain embodiments, the DNA ligase can be PBCV-1 DNA Ligase or T4 DNA ligase or T4 RNA ligase. The DNA ligase can ligate the 3' hydroxyl end to 5' phosphate end of adjacent cDNA stand(s) to form cccDNA. Again, the reaction can be cleaned up with SPRI beads and eluted in an appropriate buffer solution or water. In order to digest and remove the complementary RNA strands in the RNA:cDNA heteroduplexes (thus leaving single-stranded linear cDNA and cccDNA) the ligation products can be treated with a Ribonuclease (RNase), for example, RNase H.

In order to digest and remove single-stranded linear cDNA (leaving only cccDNA), the ligation products can be treated with an exonuclease that digests linear DNA, such as Exonuclease I or T5 Exonuclease. This nuclease can digest either single-stranded, double stranded, or both DNA molecules but should generally have only exonuclease activity to avoid digestion of the circular cDNA product. A reaction mixture, composed of ligation products and one or more of an RNase, a nuclease, and optionally an appropriate reaction buffer can be incubated at a temperature at which the enzymes are enzymatically active, for example, at about 30° C. to about 60° C., or about 40° C. to about 50° C. or about 43° C. to about 47° C., or about 45° C. The length of the incubation time can be about 1 hour to about 6 hours or more for maximal linear cDNA digestion. In certain embodiments, the length of time is about 15 minutes to about 360 minutes or about 60 minutes to about 150 minutes, or about 90 minutes to about 150 minutes, or about 100 minutes to about 130 minutes, or about 120 minutes. In certain embodiments, the RNase and/or nuclease can then be heat inactivated. An example of heat inactivation is subjecting the reaction to a temperature of about 80° C. to about 95° C. for about 2 to about 30 minutes, such as at about 80° C. for about 20 minutes. The resulting products should be composed primarily of cccDNA.

The products can then be used in downstream applications, such as a φ29 amplification reaction, to increase the copy number and amount of cccDNA. In certain embodiments, the incubation time of the DNA polymerase is about 30 minutes to about 24 hours, or about 60 minutes to about 10 hours, or about 120 minute to about 6 hours, or about 200 minutes to about 5 hours, or about 240 minutes, at a temperature of from about 20° C. to about 37° C., or about 25° C. to about 35° C., or about 28° C. to about 32° C., or about 30° C.

Useful strand displacement DNA polymerases are bacteriophage φ29 DNA polymerase (U.S. Pat. Nos. 5,198,543 and 5,001,050 to Blanco et al.), Bst large fragment DNA polymerase (Exo(−) Bst; Aliotta et al., *Genet. Anal. (Netherlands)* 12:185-195 (1996)) and exo(−)Bca DNA polymerase (Walker and Linn, *Clinical Chemistry* 42:1604-1608 (1996)). Other useful polymerases include phage φPRD1 DNA polymerase (Jung et al., *Proc. Natl. Acad. Sci. USA* 84:8287 (1987)), exo(−)VENT® DNA polymerase (Kong et al., *J. Biol. Chem.* 268:1965-1975 (1993)), Klenow fragment of DNA polymerase I (Jacobsen et al., *Eur. J. Biochem.* 45:623-627 (1974)), T5 DNA polymerase (Chatterjee et al., *Gene* 97:13-19 (1991)), Sequenase (U.S. Biochemicals), PRD1 DNA polymerase (Zhu and Ito, *Biochim. Biophys. Acta.* 1219:267-276 (1994)), and T4 DNA polymerase holoenzyme (Kaboord and Benkovic, *Curr. Biol.* 5:149-157 (1995)).

Thus such methods preferentially increase and amplify the DNA copies of the original complementary circular RNA templates versus linear RNA templates.

Kits

Certain embodiments provide for kits comprising one or more of the components, reagents, etc. used to perform any of the methods disclosed herein. In certain embodiments, instructions for performing the method are included with the kit.

EXAMPLES

Example 1

Circular RNA control molecules were successfully generated and validated to help drive wide-scale confidence and enable robust scientific results for the emerging field of circular RNA study. Protocol development for circular RNA enrichment showed strong feasibility with depletion of linear RNA greater than 300-fold and selective amplification of circular RNA 17-fold.

Figure 1A:
Figure 1B:
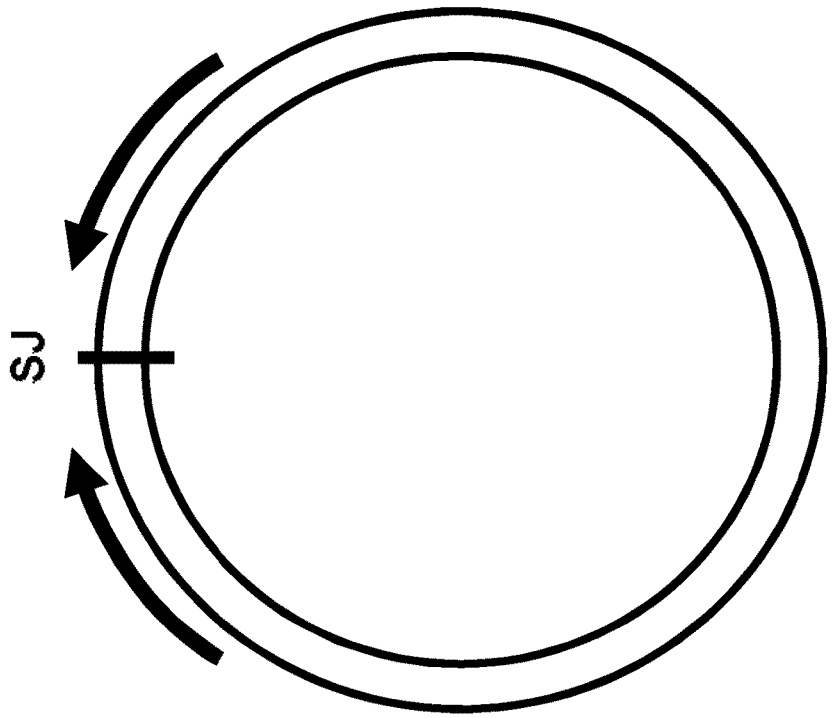
Figure 1C:
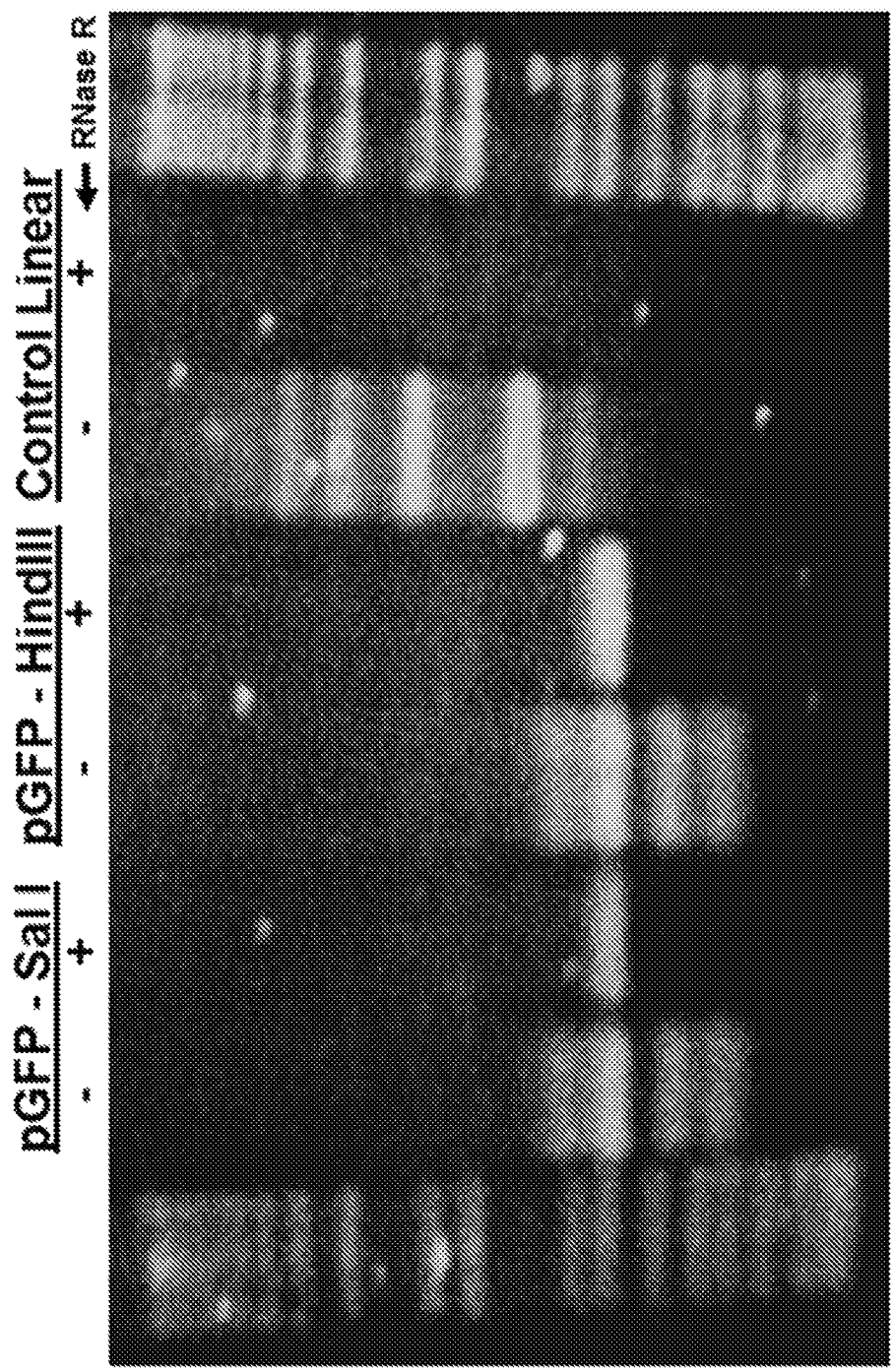
Figure 1D:
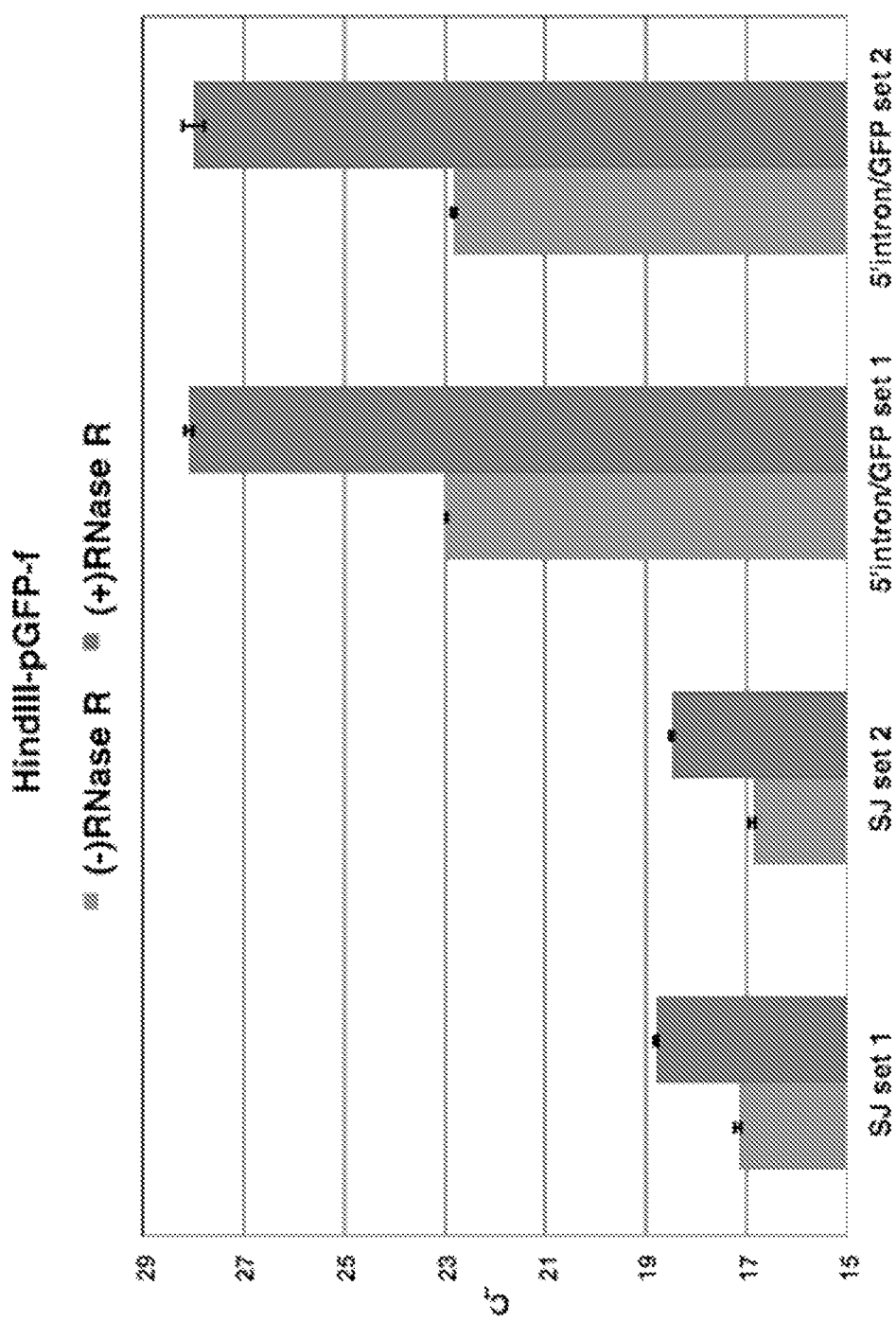

In order to develop a circular RNA control, plasmid constructs containing the open reading frame (ORF) of green fluorescent protein (GFP) were obtained from Dr. Manuel Ares (Perriman R, Ares M. Circular mRNA can direct translation of extremely long repeating-sequence proteins in vivo. *RNA* 1998; 4(9):1047-1054). The GFP ORF in these plasmid constructs are flanked by group I introns that undergo ribozyme catalyzed self-splicing to generate circular GFP RNA molecules. Linearized plasmid was in vitro transcribed (IVT) to produce self-splicing transcripts. Following in vitro splicing (IVS), a circular RNA molecule of 812 nucleotides was formed. The efficiency of IVS to form circular RNA molecules was ~20%, thus the non-spliced linear species were degraded with RNase R to generate a pool with a high ratio of circular RNA control molecules for use in protocol development and testing. The circular RNA control molecule was checked for quality using qPCR primers designed to target the 5' intron/GFP ORF junction (FIG. 1A) and a second set of primers designed against the GFP ORF splice junction (FIG. 1B). Transcripts were generated from plasmid linearized with SalI or HindIII and subjected to either mock or RNase R digestion to degrade the non-spliced linear RNA component (FIG. 1C). qPCR results showed a 15-30-fold reduction in linear non-spliced RNA versus circRNA following RNase R treatment (FIG. 1D). These results demonstrate generation of a circular RNA control molecule and measures to assure quality through custom designed SYBR Green qPCR assays. In addition, this result shows the feasibility for large-scale production of a circular RNA control, which is intended to be included, in a commercial kit. Including this control will help drive wide-scale confidence amongst users of the kit and enable robust scientific results for the emerging field of circular RNA study.

i. TaqMan Assays Show High Specificity for Targets

Figure 2:
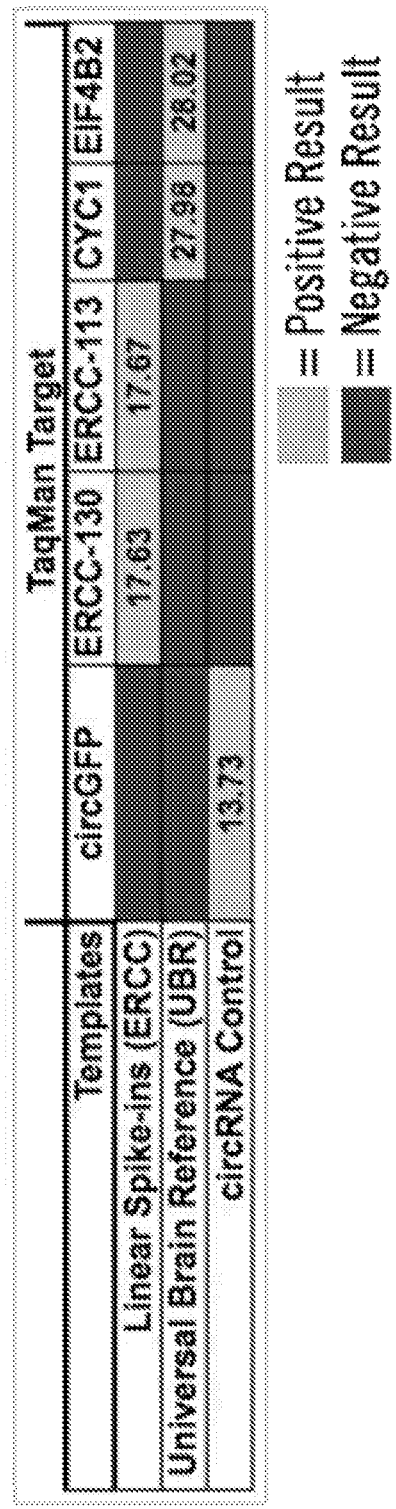
Figure 3:
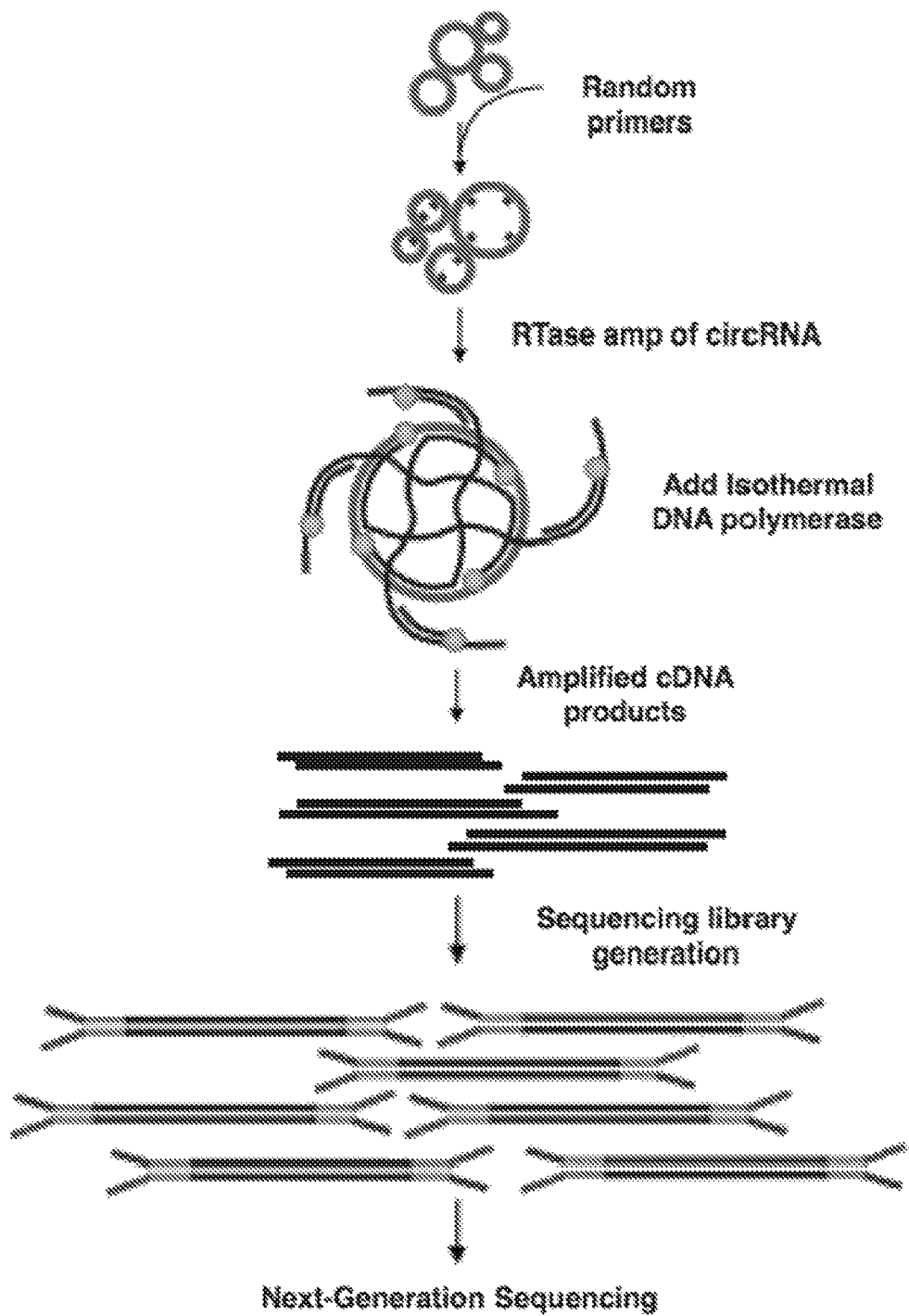

In order to accurately assess the success and failures of experiments, custom TaqMan assays were designed against two linear spike-in controls from the ERCC set (ERCC0113 and ERCC0130), two genes endogenous to UBR (CYC1 and EIF4A2), and the splice junction of the circular RNA control (circGFP). TaqMan target specificity was assessed using a "cross-talk" experiment, where every TaqMan control probe was run against every target. Results showed extremely high specificity for each probe/target set with no detectable signal from non-specific targets (FIG. 2). This key assay allows clean and separate quantification of linear and circular RNA control molecules.

ii. Comparison of Linear Depletion Strategies

Circular RNA molecules have been shown to exist at approximately 1% of mRNA levels (~0.02% of total RNA). Thus, a comparison of linear depletion methods would be most informative if a test RNA pool or mixture were used that contained circular RNA controls approaching biological levels. To this end, an RNA test mixture was created consisting of UBR with linear and circular RNA control spike-ins for use in the comparison of linear depletion methods. For these initial experiments, the circular RNA concentration in the test RNA mixture was 0.2%.

Current linear depletion protocols for circular RNA enrichment use 20-60 micrograms of total RNA material (Jeck, W. R., et al., Circular RNAs are abundant, conserved, and associated with ALU repeats. RNA, 2013. 19(2): p. 141-57.), which in most cases is much higher than the amount available from research or clinical samples. Thus, we chose to test linear depletion methods at input levels of 1 microgram total RNA, well within the range of input material used for next-generation RNA-sequencing experiments. The level of circular RNA in this mixture was 2 nanograms (0.2%).

iii. Evaluation of Circular RNA Enrichment Conditions and Next-Generation Sequencing with Total RNA from Whole Brain.

Initial evaluation of circular RNA shows 16-fold increase in target molecule quantity. The polymerase BTB3 was specifically selected because it has been reported to function isothermally, and possess both RNA-directed (reverse transcriptase) and DNA-directed DNA polymerase activities, as well as strand displacement activity.

Figure 6A:
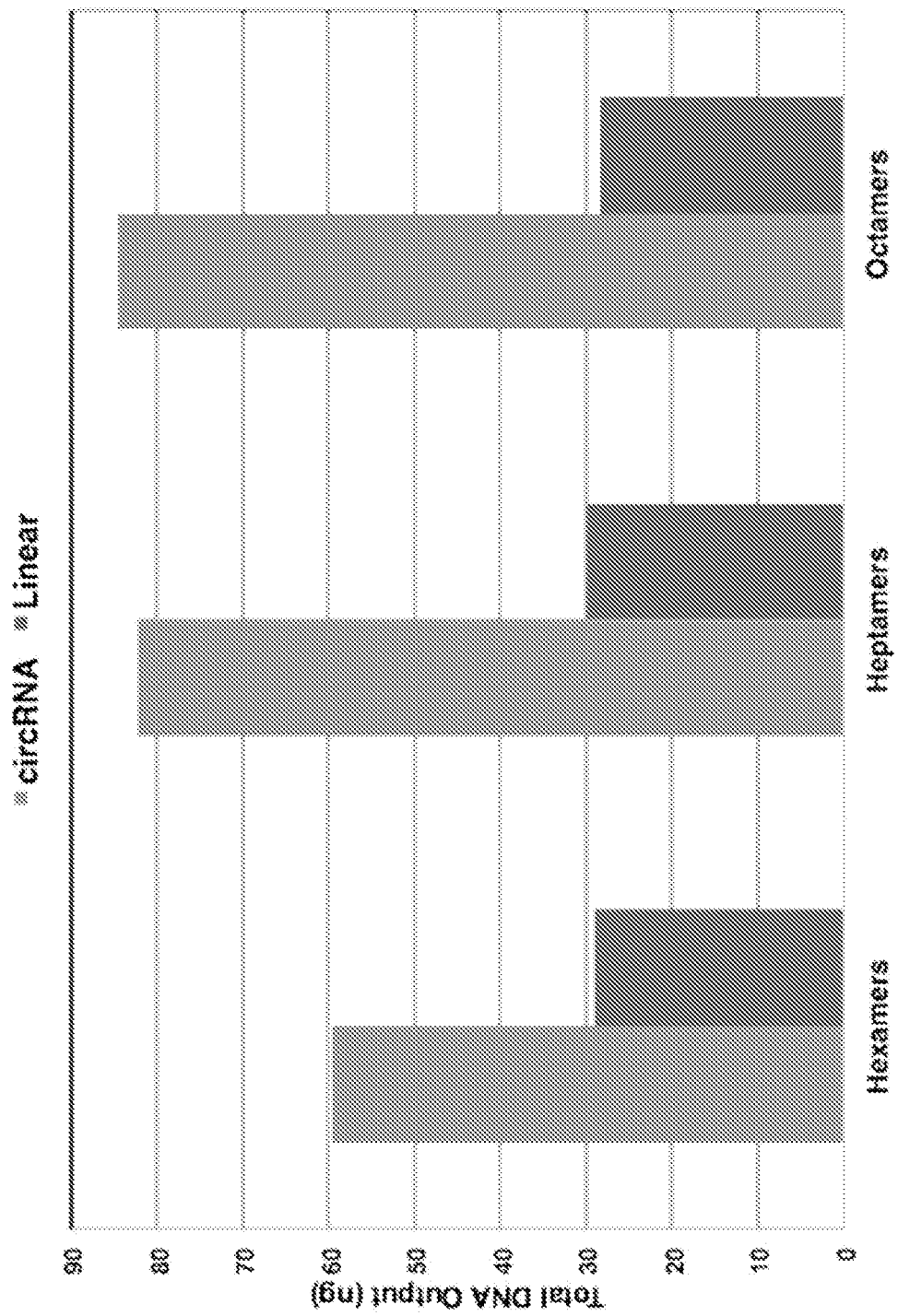
FIG. 6B is a graphical representation showing fold amplification of circular RNA input (5 ng) for each primer type shown in FIG. 6A.
Figure 6B:
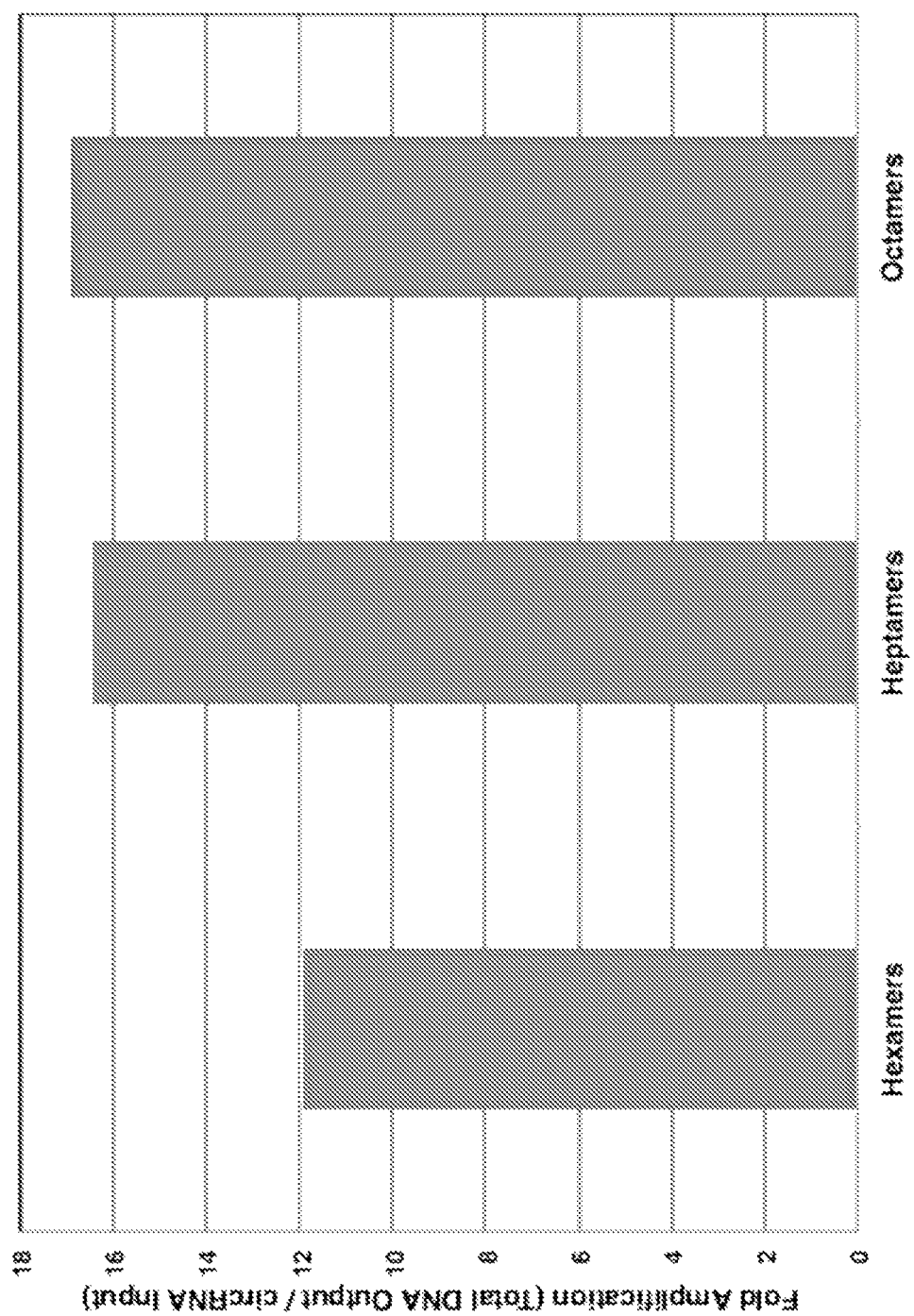

In order to identify a method/enzymes favoring circular RNA over linear species, test amplifications were performed on 10 nanogram inputs of linear and circular RNA control species separately. Single-enzyme, single-step amplifications were performed using BTB3 and 10 nanograms of each amplification test mix (linear and circular RNA controls). Initial experiments showed little preferential amplification of circular RNA molecules with BTB3 alone. A dual-enzyme amplification procedure was then tested employing a reverse transcriptase and BTB3. Amplification of circular RNA molecules using a single-step, dual-enzyme mix, employing RTx+BTB3 or PSII+BTB3 achieved circular RNA amplification of approximately 2-fold. In addition, ProtoScript II showed a preference for circular RNA amplification versus RTx. In order to reach additional levels of circular RNA amplification, a two-step, dual-enzyme procedure was tested where cDNA was first generated using either RTx or PSII and then BTB3 was added to the reaction to drive amplification of cDNA produced during the previous reverse transcription step. This two-step strategy, starting with 10 nanograms of input RNA, showed an approximate 4-fold preferential amplification of circular RNA molecules over linear using initial reverse transcription by PSII followed by addition of BTB3 (PSII→BTB3) (FIG. 6A). Minor initial optimizations were performed; including increased incubation times, temperatures, and varied length of random primers for amplification. A two-step reaction of PSII→BTB3, using random octamer primers exhibited a ~17 fold increase in DNA output from 5 nanograms circular RNA input. These results show the feasibility of preferential amplification of circular RNA over linear RNA using PSII+ BTB3 in a two-step, dual-enzyme method (FIG. 6B).

Example 2

Circular RNA to Circular DNA Conversion Followed by Linear and Circular RNA Removal or Reduction.

Figure 4:
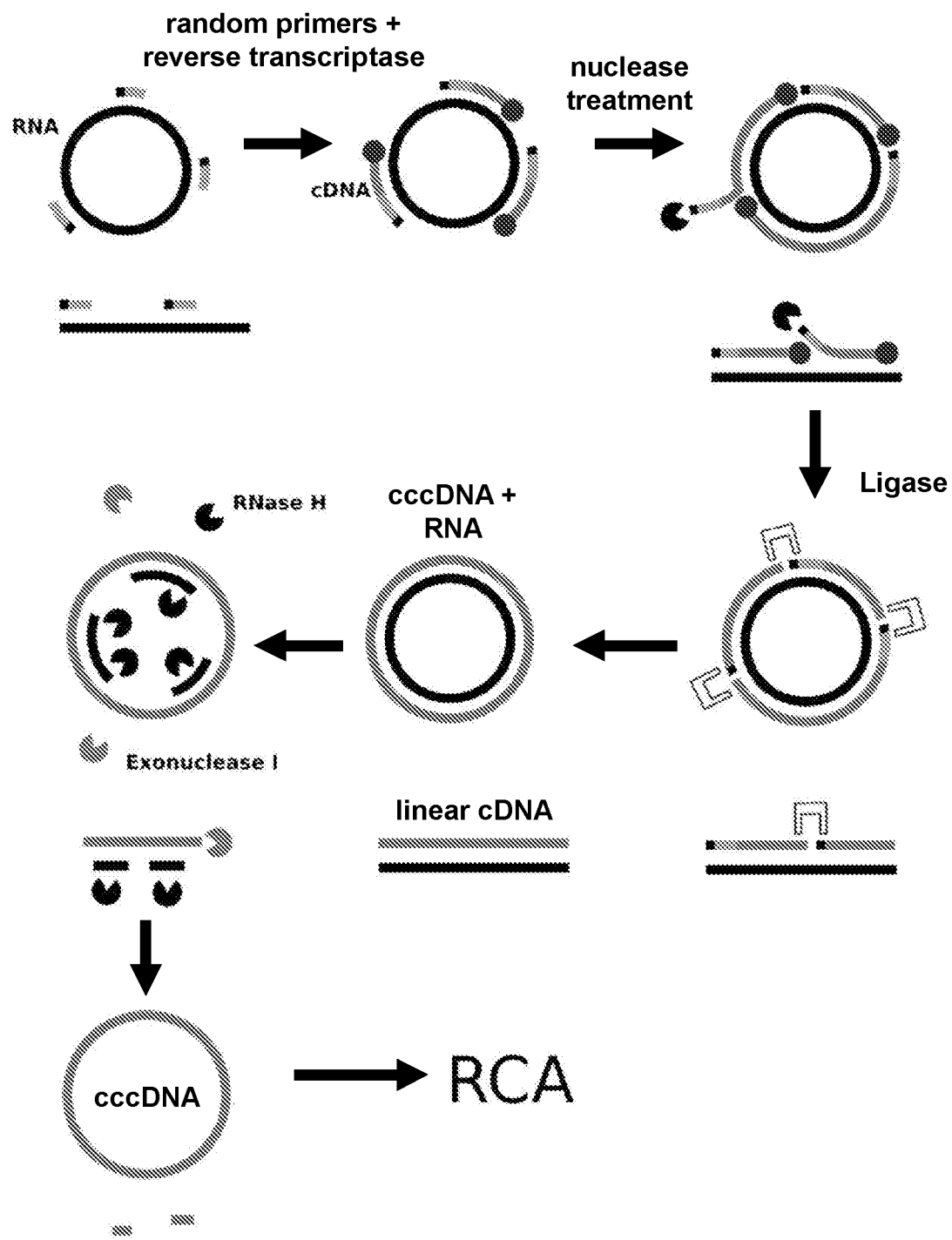
Figure 5A:
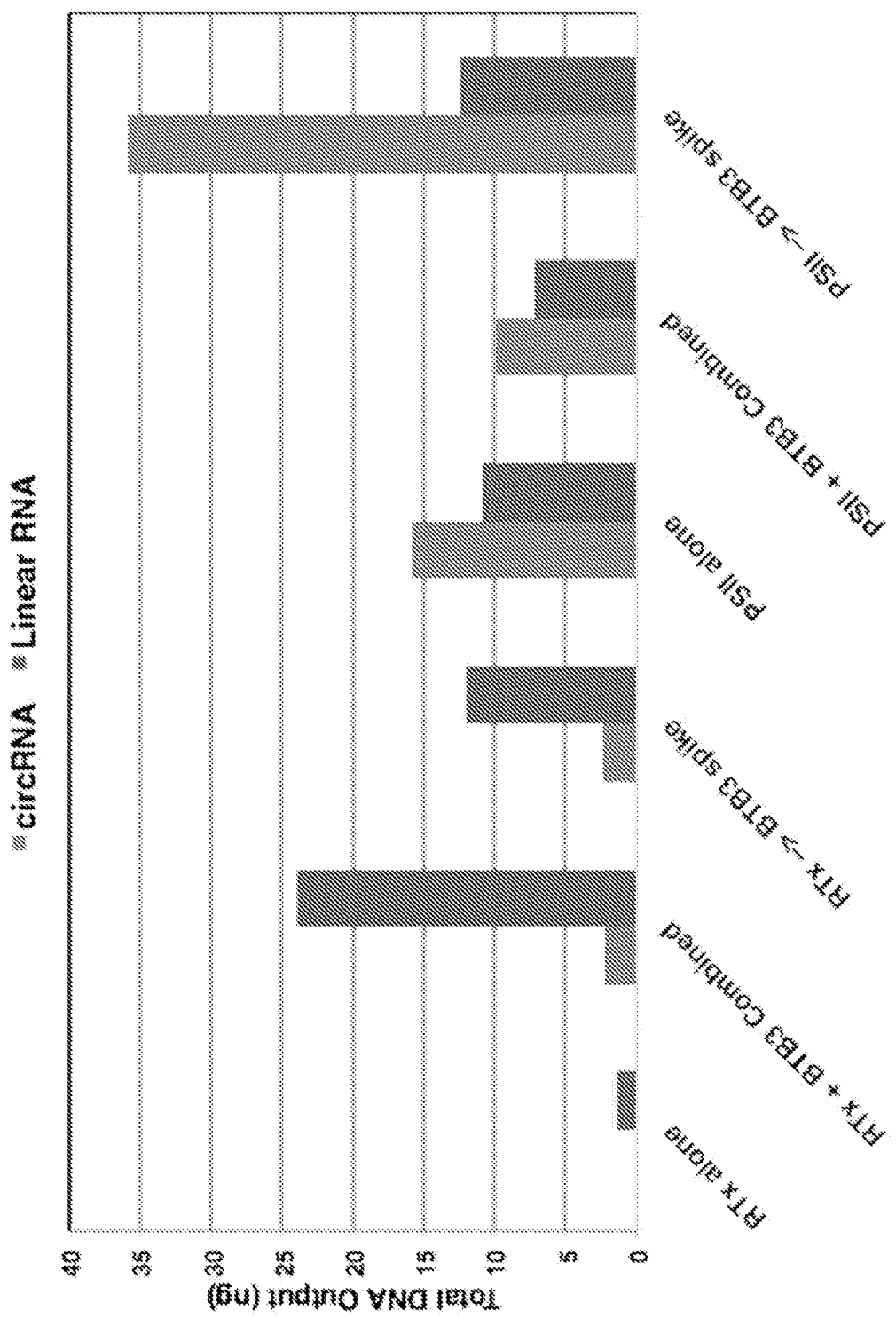
Figure 5B:
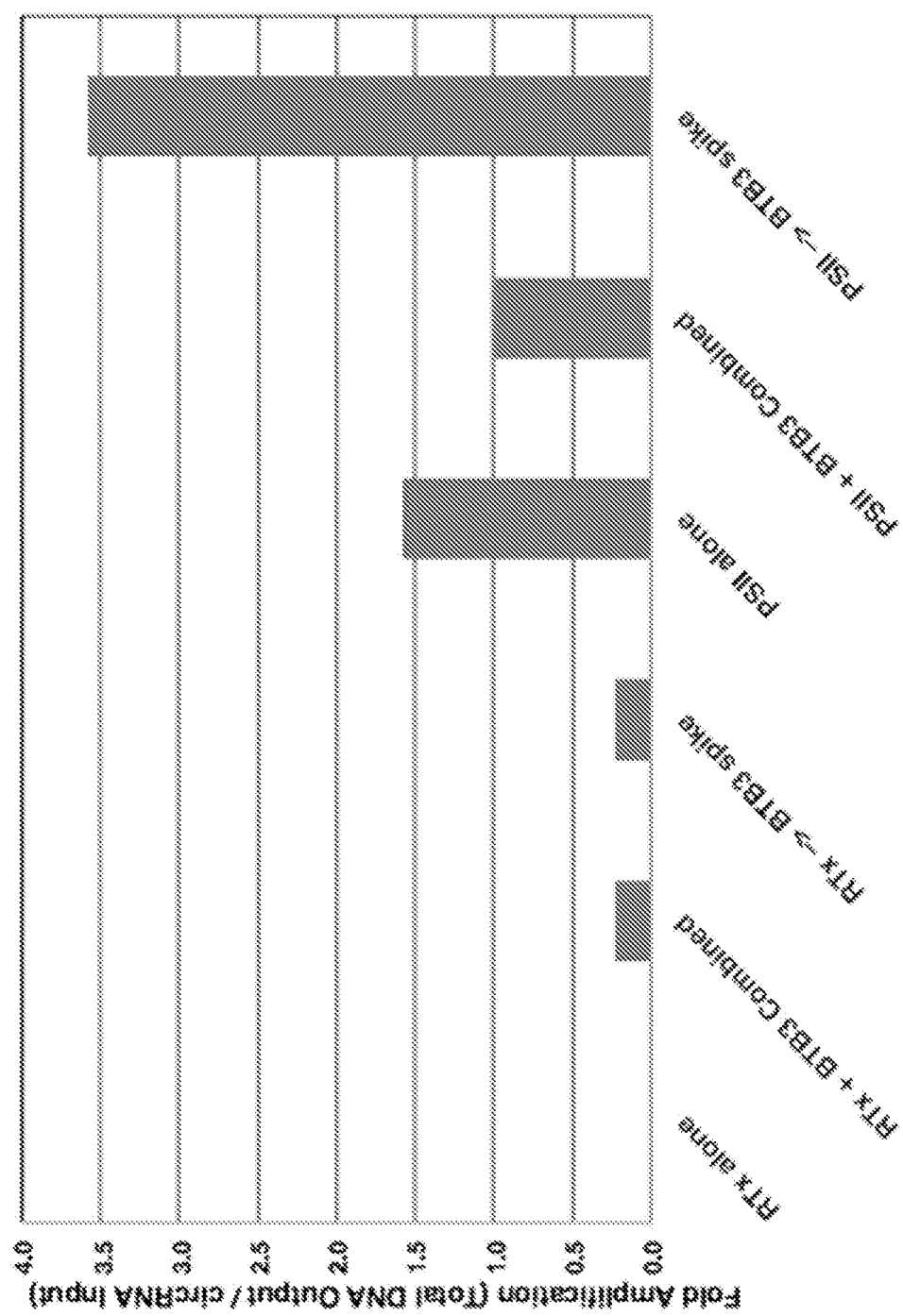

The method in the diagram of FIG. 4 uses a circular RNA molecule as the target/scaffold and illustrates one embodiment of generating circular DNA copy molecule(s) from a corresponding circular RNA template. Starting at the top left of FIG. 4, synthesis of complementary cDNA sequence by reverse transcription was performed using the following reaction components: RNA from 3 µg of ribosome-depleted total RNA in 1× Protoscript II® buffer (NEB) supplemented with 100 ng 5'-phosphorylated random oligonucleotide octamer primers, 0.5 mM dNTP mix and water for a total reaction volume of 12.5 µl. The mixture was denatured at 65° C. for 5 minutes and then quick-chilled on ice (~0° C.). The following was added on ice: 10 mM DTT, 20 U RIBOLOCK® RNase inhibitor (Thermo), and 200 U Protoscript II reverse transcriptase (NEB) in a final volume of 20 µl. The components were incubated for 10 min at 25° C., followed by 50 minutes at 42° C. The reaction was brought to a final volume of 40 µl with the addition of $H_2O$, cleaned up with 72 µl (1.8×) SPRI® beads (Agencourt), and finally eluted with 45 µl $H_2O$. This was followed by enzymatic degradation of single-stranded DNA by a nuclease (top right) with 44 µl cDNA reaction products, 10×MBN buffer (NEB) (5 µl), and Mung Bean Nuclease (0.2 U/µl at 1 µl). This mixture was incubated for 30 minutes at 30° C., followed by addition of 0.5 µl of 1% SDS, and SPRI® (Agencourt) clean up with 90 µl beads (1.8×). The products were eluted with 27 µl of $H_2O$. The middle right of FIG. 4 shows ligation of adjacent, single-stranded cDNA bridged by the complementary circular RNA template performed with MBN reaction products, adding 10× SPLINTR® buffer (NEB) (3 µl), and adding SPLINTR® ligase (NEB) (10.3 µM and 1 µl). This mixture was incubated for 15 minutes at 25° C., and then cleaned up with SPRI® (Agencourt) 54 µl beads (1.8×), eluted with 17 µl of $H_2O$.

As show in the middle center of FIG. 4, a covalently closed circular cDNA molecule (cccDNA) of the same sequence as the circular RNA template is formed at this point. This can be followed by endoribonuclease digestion of circular RNA hybridized to the circular DNA copy and linear RNA hybridized to linear DNA copies including digestion of linear DNA by a nuclease (middle left). This was accomplished by taking 16 µl of products from the SPLINTR® (NEB) ligation process, and adding 10× HYBRIDASE® buffer (2 µl) (Epicentre), HYBRIDASE® (Epicentre) (5 U/µl at 1 µl), and Exonuclease 1 (Epicentre) (20 U/µl at 1 µl) for a total reaction volume of 20 µl. This mixture was incubated at 45° C. for 2 hours, followed by heat inactivation of Exo I by 20 minutes at 80° C. The result is a product that has been enriched for single-stranded circular DNA copies of the original circular RNA templates (bottom left).

Figure 7:
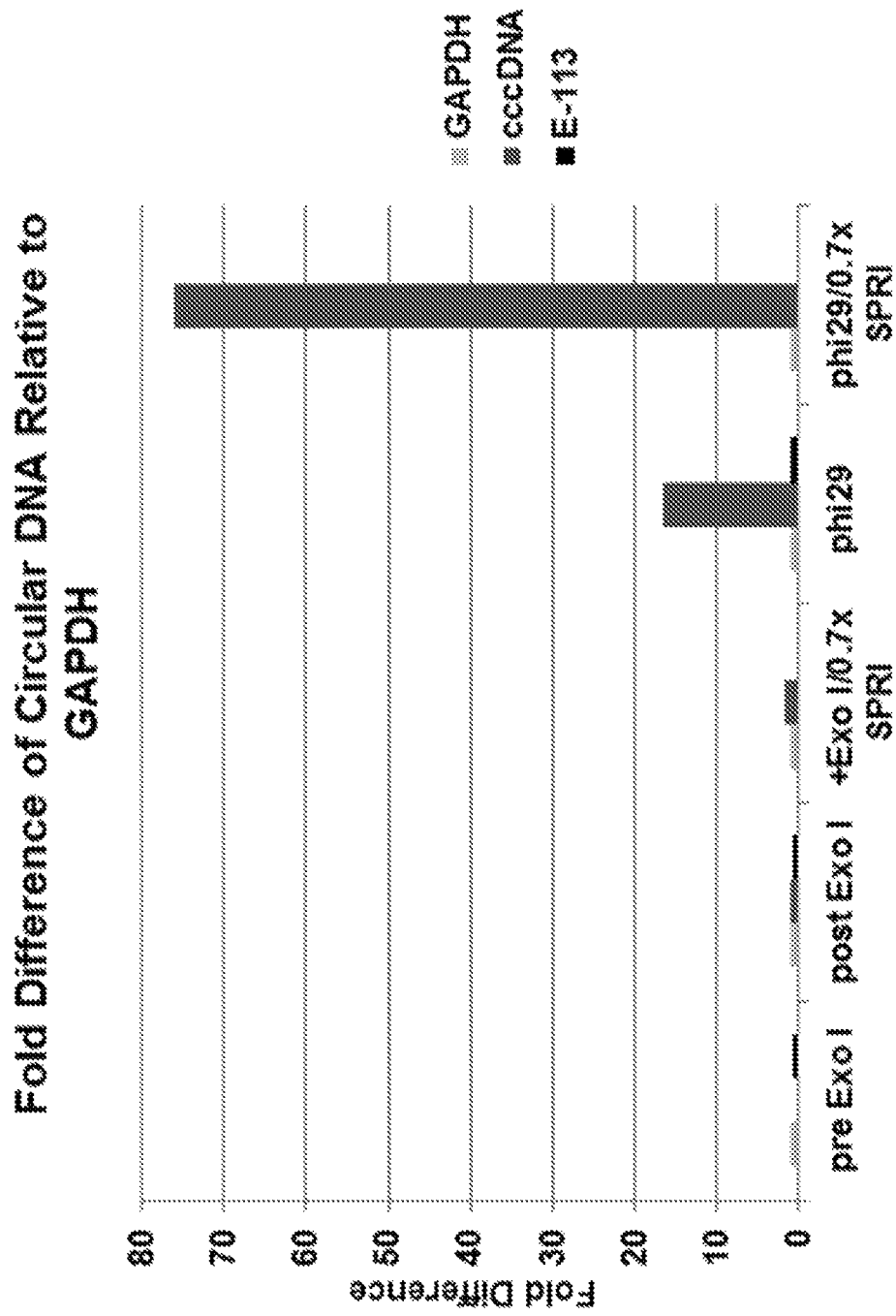
FIG. 7 shows quantitative PCR (qPCR) results that evidence the formation of covalently closed circular DNA copy molecules from known circular RNA control molecules.

FIG. 7 shows quantitative PCR (qPCR) results that prove the formation of covalently closed circular DNA copy molecules from known circular RNA control molecules. A control RNA mix was used which included 1 microgram Human Universal Brain Reference RNA, 10 picogram circGFP RNA control (0.001%) and ERCC linear RNA control. qPCR probes were designed against the known backsplice junction contained in the circular GFP RNA control (circGFP) and had no similarity to the human genome nor a linear form of the control. Thus, a positive qPCR signal would only be detected from cDNA molecules (exhibiting the backsplice junction) synthesized from the original circular GFP RNA control template containing the backsplice junction. In addition, the accumulation of circular cDNA molecules, during rolling circle amplification with φ29, would only occur if the cDNA molecules were covalently closed circular cDNA. In order to measure the levels of endogenous and exogenous linear control transcripts for fold-change determination, additional qPCR probes were designed against the transcript sequence for Glyceraldehyde-3-Phosphate Dehydrogenase (GAPDH) and one of the ERCC linear RNA control transcripts (E-113). The control RNA mix was treated with the method shown in FIG. 4 and sample aliquots were collected pre-exonuclease treatment, post exonuclease treatment, post exonuclease treatment with a magnetic bead DNA cleanup step (+Exo 1/0.7× SPRI® Agencourt), following amplification of the circular DNA copy molecules by an isothermal polymerase (φ29), and following amplification of the circular DNA copy molecules by an isothermal polymerase (φ29) and a magnetic bead DNA cleanup step (φ29/0.7× SPRI® Agencourt). The magnetic bead cleanup was used to remove smaller cDNA products and digestion fragments from the mixture, which could give a qPCR signal if they contained the backsplice junction of the circGFP RNA control. Results show that circGFP cDNA backsplice sequences were greater than 70× more abundant, following rolling circle amplification with φ29/0.7× SPRI cleanup, as compared to the linear transcripts for GAPDH and ERCC 113. Thus, proving cDNA copies of the circGFP control templates were generated in a sequence specific manner and the adjacent cDNA ends were ligated to form covalently closed circular cDNA molecules.

Figure 8:
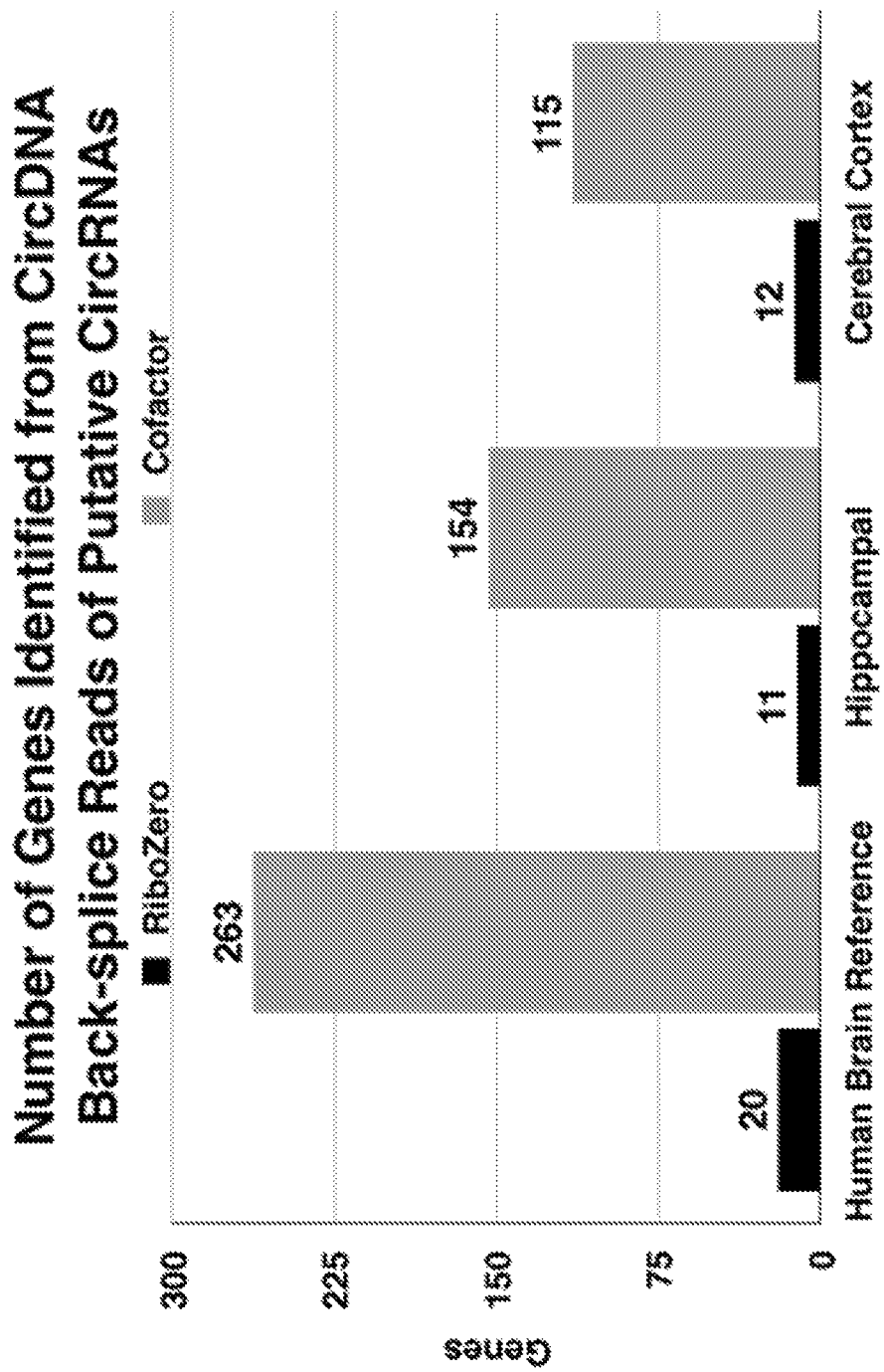
FIG. 8 show bioinformatic sequence analysis results evidencing that circular DNA molecules were generated from circular RNA present in Human Hippocampal and Cerebral Cortex brain tissues.

FIG. 8 shows a duplicate set of Human Brain Reference, Hippocampal, and Cerebral Cortex RNA samples were subjected to either ribosomal transcript reduction (black bars; RIBOZERO® Epicentre) or the current embodiment (gray bars). The samples with ribosomal transcripts removed were subjected to next-generation sequencing RNA library preparation and sequencing to produce data for bioinformatic analysis. The second set of samples, treated with the current embodiment, were isothermally amplified using φ29 and subjected to next-generation sequencing DNA library preparation and sequencing to produce data for bioinformatic analysis. The resulting sequence data was analyzed using the bioinformatic analysis method "CIRI" (Gao, Y, Wang, J and Zhao F. CIRI: an efficient and unbiased algorithm for de novo circular RNA identification. *Genome Biology* 2015, 16:4). CIRI identifies signatures (specifically backsplice junctions and GT-AT splicing signals), embedded in the sequence data, specific to circular DNA molecules constructed from circular RNA molecules. The samples treated with the current method exhibited greater than 10-fold more circular RNA backsplice signals demonstrating that circular DNA molecule can be constructed and amplified from endogenous circular RNA molecules contained in biological samples.

Figure 9:
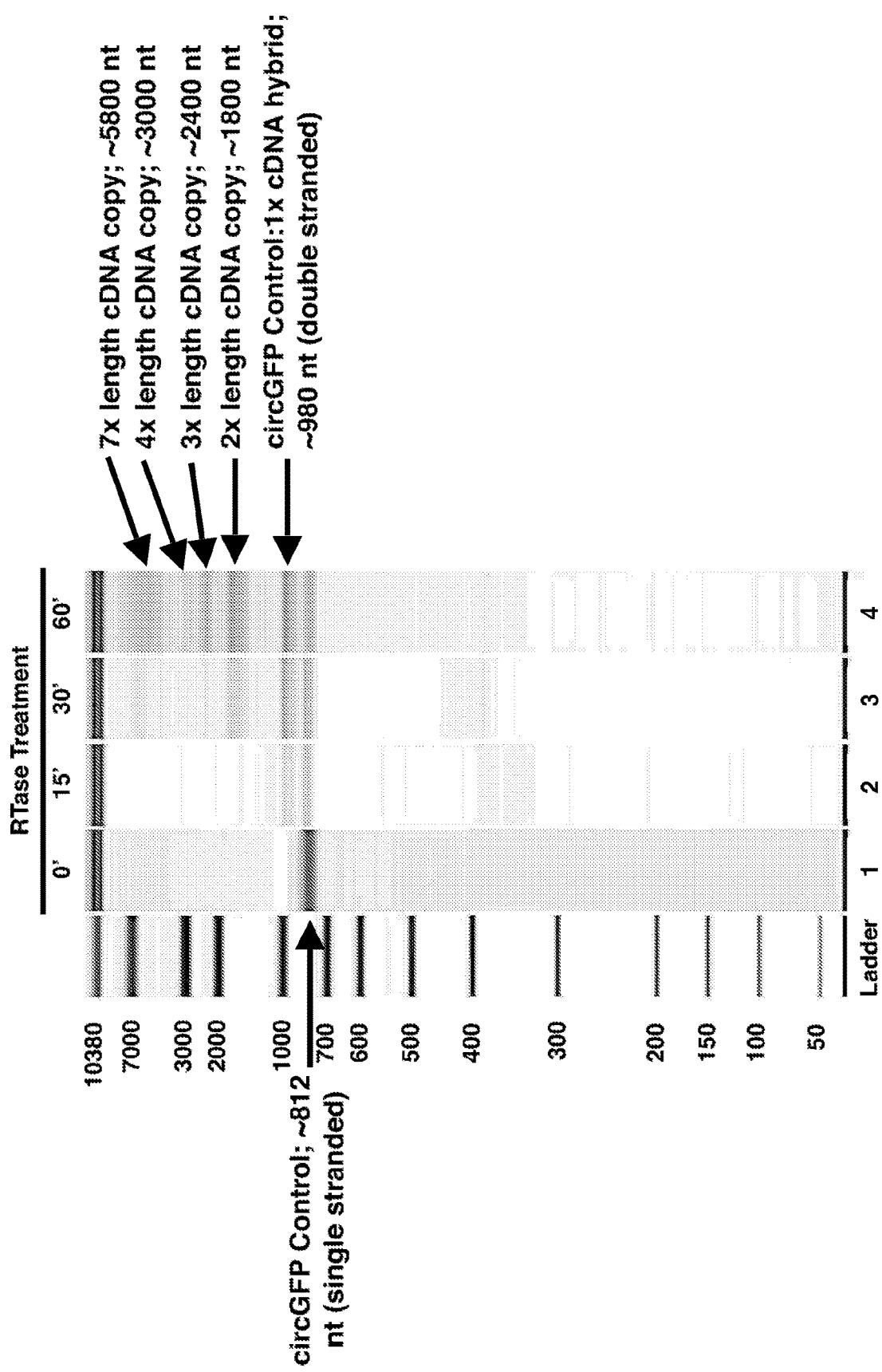
FIG. 9 is a gel demonstrating that rolling circle cDNA replication of circular GFP RNA control increases with greater incubation times.

FIG. 9 shows rolling circle cDNA replication of circular GFP RNA control increases with greater incubation times. Circular GFP RNA control (circGFP) was incubated with PROTOSCRIPT II (NEB) for 0, 15, 30 and 60 minutes at 42° C. (lanes 1-4). At t=0 (lane 1), a single band is observed closely corresponding to the size of the circGFP molecule (812 nt). At t=15' (lane 2), a secondary band is observed, in addition to circGFP, which closely correlates to the expected size of a circGFP Control: 1× cDNA hybrid heteroduplex formed by ProtoScript completing one cDNA copy around the circGFP RNA control molecule. At increasing incubation times (lanes 3 and 4) additional bands appear which increase in size and closely correspond to those expected for multiple rolling circle cDNA copies of circGFP by ProtoScript II and indicate that linear circRNA cassette copies (n+1) are produced the method.

Example 3 i. Assay to Confirm Ligation Activity and T5 Exonuclease Flap Removal.

Figure 10A:
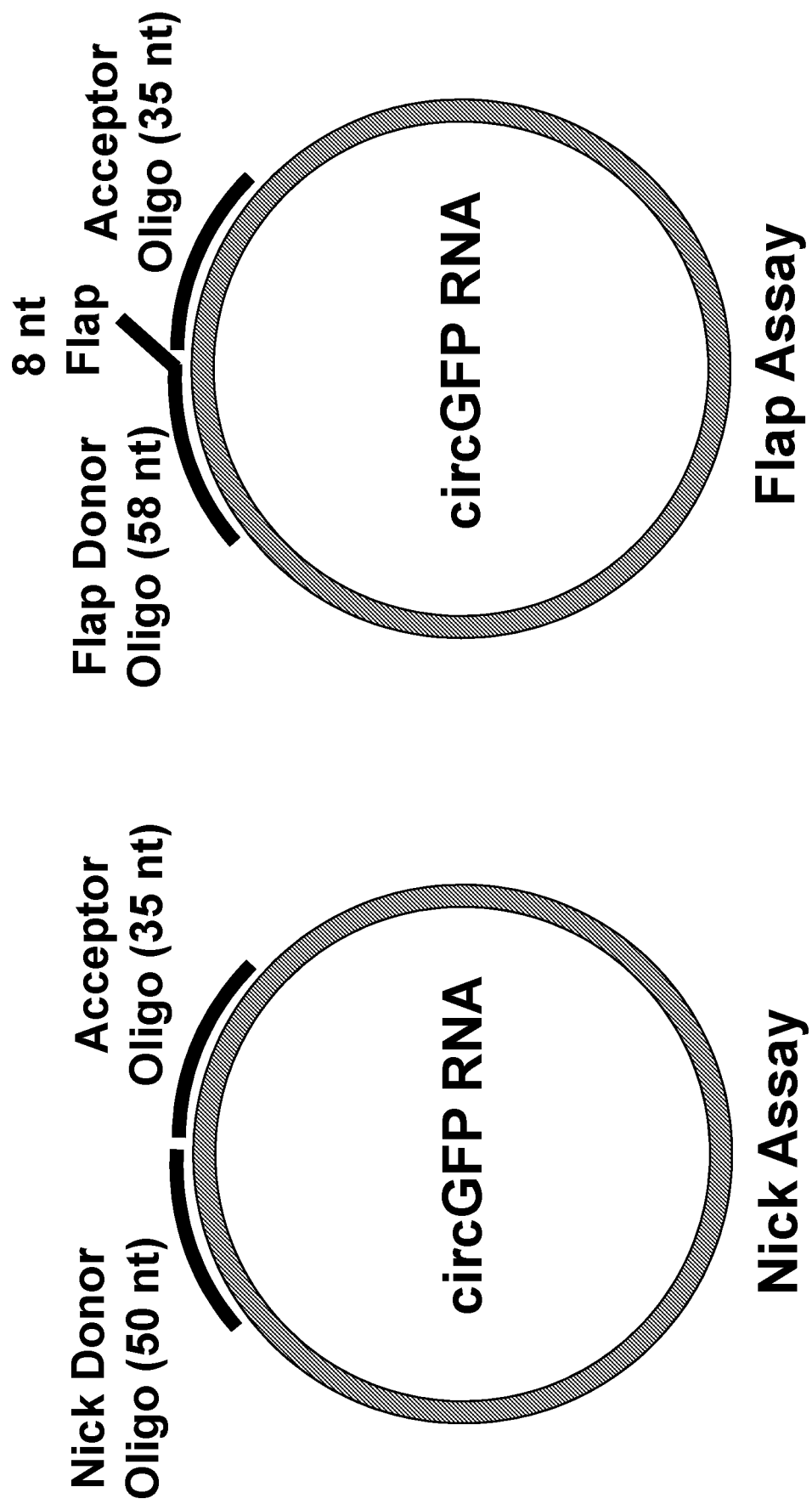
FIG. 10A is a schematic diagram of the strategy used to assay flap removal for the generation of ligatable DNA ends.

FIG. 10A is a schematic diagram of the strategy used to assay flap removal for the generation of ligatable DNA ends. Two separate assays were performed, a control nick assay (left) and experimental flap assay (right). For the nick assay, 5'-phosphorylated nick donor DNA oligonucleotides (50 nucleotides [nt]) and 3'-hydroxyl acceptor DNA oligonucleotides (35 nt) were first hybridized to the circular GFP RNA control (circGFP RNA) in equimolar amounts. Following hybridization, a nick donor DNA oligonucleotide would be annealed directly downstream and adjacent to an acceptor oligonucleotide, separated only by a nick, thereby providing a ligatable substrate for a ligase. For the flap assay, flap donor DNA oligonucleotides (58 nt) and acceptor DNA oligonucleotides (35 nt) were hybridized with the circular GFP RNA control (circGFP RNA) in equimolar amounts. The difference between the flap donor oligonucleotide and the nick donor oligo is the presence of an additional 8 base sequence extension at the 5' end of the flap donor oligonucleotide. Thus, the flap assay (right) models cDNA flaps that would result from strand displacement activity during reverse transcription of circular RNAs. The flap assay oligonucleotides hybridized to the circular GFP control RNA will only provide a ligatable substrate for a ligase after complete removal of the 8 nucleotide donor oligo flap to form a nick between the donor and acceptor oligonucleotides. The removal of more than 8 nucleotides from the flap donor oligonucleotide will result in a gap not allowing ligation by a ligase enzyme. After treatment with PBCV-1 DNA ligase, samples were heat-denatured and run on a 4% agarose gel. The presence of an 85 nt band indicates the successful ligation of donor and acceptor oligonucleotides (35 nt+50 nt=85 nt positive ligation product).

ii. Flap Removal by T5 Exonuclease Creates Ligatable Ends.

Figure 10B:
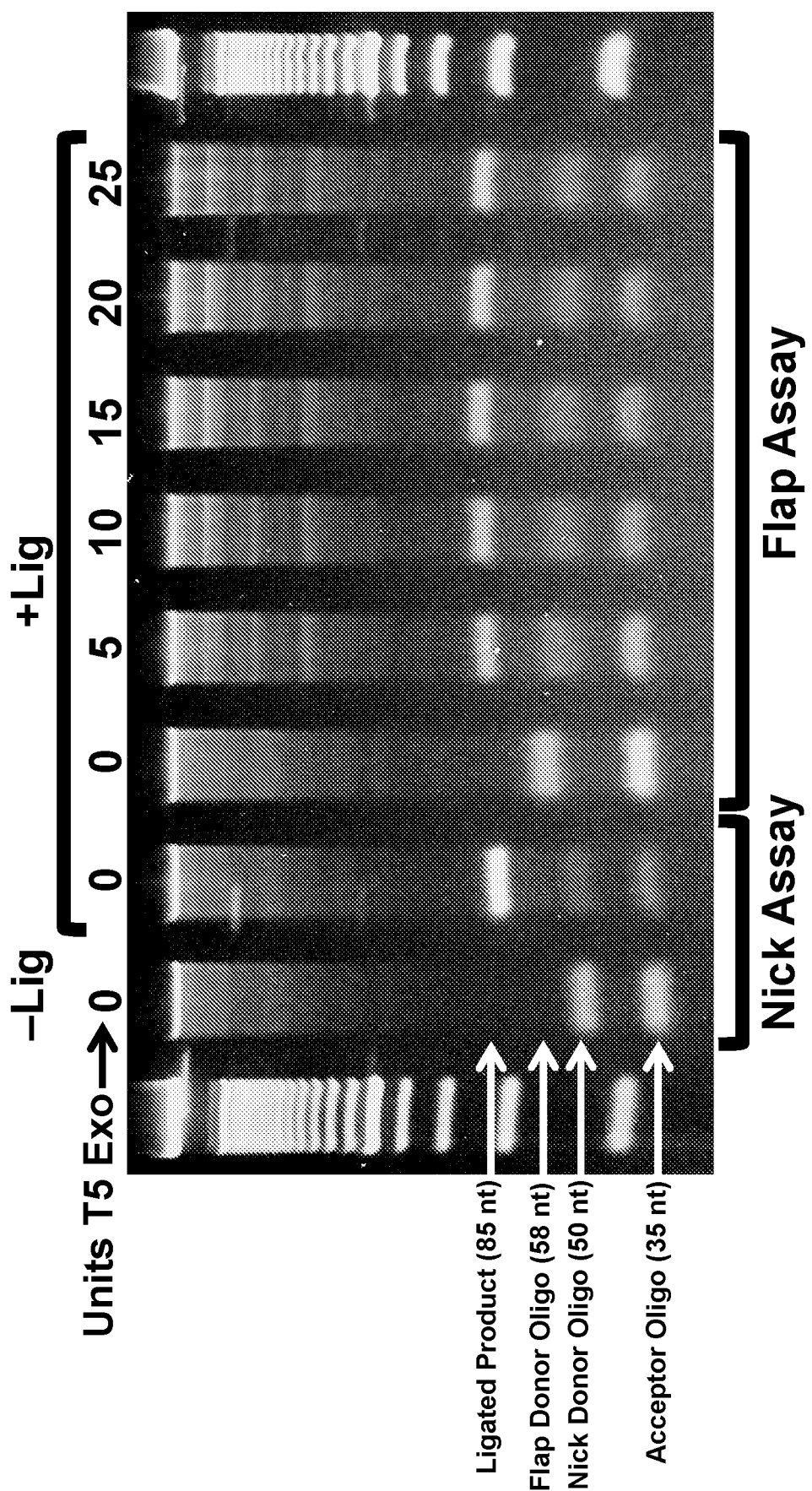
FIG. 10B shows a gel demonstrating flap removal by T5 exonuclease to create ligatable ends.

FIG. 10B shows a gel demonstrating flap removal by T5 exonuclease to create ligatable ends. Nick assay oligonucleotides were annealed to circular GFP RNA control (FIG. 10A, left) and then treated with or without PBCV-1 DNA ligase before heat denaturation and analysis by gel electrophoresis. In the absence of ligase, only the 35 nt acceptor 50 nt nick donor oligonucleotides are detected, as indicated by lane 2. After PBCV-1 DNA ligase treatment of the nick assay, the expected 85 nt band corresponding to the ligation product is observed in lane 3. Flap assay oligonucleotides were similarly annealed to circular GFP RNA control (FIG. 10A, right), but subjected to treatment with increasing amounts of T5 exonuclease (from 0 to 25 units), prior to incubation with PBCV-1 DNA ligase. In the absence of treatment with T5 exonuclease, PBCV-1 DNA ligase does not produce a 85 nt band corresponding to a ligation product and only the 35 nt acceptor and 58 nt flap donor oligonucleotides are observed (lane 4). In contrast, treatment of the flap assay with T5 exonuclease prior to treatment with PBCV-1 DNA ligase results in detection of an 85 nt band corresponding to the ligation product (lanes 5-9). These results show that T5 exonuclease is capable of removing 5' DNA flaps and creating a ligatable nick, from a DNA:RNA hybrid branch. Size markers (lanes 1 and 10) are the E-GEL® 25 bp DNA Ladder (Invitrogen). Note that the size markers are double-stranded (units in basepairs), and the assay oligos are single-stranded (units in nucleotides).

iii. Amplification Cassette Concatemers Generated from Rolling Circle Amplification of Circular DNA Control.

FIG. 11A is a graphic depiction of concatemers and a single cassette generated by rolling circle amplification of covalently closed circular DNA (cccDNA circGFP) generated from the circular GFP control RNA. The relative positions of three different unique restriction enzyme recognition sites are indicated (NcoI, MfeI and SacI) as well as the cccDNA circGFP backsplice junction (1 . . . 2 Backsplice Junction).

iv. In Silico Double Restriction Enzyme Digest of circGFP Cassette.

FIG. 11B shows the result of an in silico double restriction enzyme digest of the circular GFP cassette with SacI and MfeI (top), or with SacI and NcoI (bottom). The predicted restriction enzyme fragments for the SacI/MfeI digest are 640 bp and 172 bp and the predicted fragments for the SacI/NcoI digest are 566 bp and 172 bp.

v. Restriction Enzyme Analysis of φ29 Reaction Products.

FIG. 11C shows restriction enzyme analysis of φ29 polymerase reaction products derived from amplification of the cccDNA circGFP generated from the circular GFP control RNA. Amplification of a covalently closed circular DNA template with φ29 polymerase is expected to yield high molecular weight DNA products comprised of concatemers containing tandem repeats representing the original circular GFP control RNA template. Restriction enzyme digestion of these amplification products, using a unique restriction enzyme, would produce a predominant fragment the same size as the repeating cassettes comprising the amplified concatemer cassette products. Lane 2 shows high molecular weight DNA from a φ29 amplification reaction that was not treated with restriction enzyme digestion (UC). Lanes 3, 4 and 5 demonstrate that digestion of the φ29 reaction products with three different enzymes (SacI, MfeI or NcoI, respectively) results in a single major band the same size as the circular GFP cDNA cassette (812 bp). Double digestion with SacI and MfeI (lane 6; SacI+MfeI) or SacI and NcoI (lane 7; SacI+NcoI) yields the expected pattern of fragments shown in the in silico double restriction enzyme digest results (FIG. 11B). These results show covalently closed circular DNA molecules were generated from the original circular GFP RNA control template and are effectively amplified by φ29 polymerase. Size markers (lanes 1 and 10) are the E-GEL® 25 bp DNA Ladder (Invitrogen). Note that the size markers are double-stranded (units in basepairs), and the assay oligos are single-stranded (units in nucleotides).

vi. φ29 Amplification Products from Covalently Closed Circular DNA Molecules.

FIG. 12 shows the increase in φ29 amplification products from covalently closed circular DNA molecules. The circular GFP RNA control was subjected to reverse transcription, followed by flap removal with T5 exonuclease. Identical aliquots were then processed in parallel reactions with either PBCV-1 DNA ligase or buffer. Next, each of these samples, including a no template control, was processed in parallel φ29 polymerase amplification reactions. Reaction aliquotes were removed at increasing time points and assayed for DNA concentration using the Qubit fluorometric assay (Thermo Fisher). If covalently closed circular DNA molecules were generated from the circular GFP control molecule, they would resist exonuclease digestion and act as amplification templates for φ29. The sample treated with PBCV-1 DNA ligase (+PBCV-1 DNA ligase) showed a significantly greater rate of increase in DNA amplification products than the buffer control reaction (−PBCV-1 DNA ligase) or the no template control (NTC). These results show that DNA flaps were successfully removed with T5 exonuclease and covalently closed circular cDNA copies of the circGFP RNA control were generated serving as templates for rolling circle amplification.

The breadth and scope of the present disclosure should not be limited by any of the above-described exemplary embodiments, but should be defined only in accordance with the following claims and their equivalents.

What is claimed is:

1. A method of constructing a covalently closed circular cDNA molecule, the method comprising
    ligating with a ligase one or more linear cDNA fragments bound to an endogenous circular RNA molecule scaffold, wherein the one or more linear cDNA fragments and the endogenous circular RNA molecule scaffold form an endogenous circRNA-DNA heteroduplex, to convert the one or more linear cDNA fragments into the covalently closed circular cDNA molecule, thereby constructing the covalently closed circular cDNA molecule which has the circular structure of the endogenous circular RNA molecule scaffold.

2. The method of claim 1, wherein the ligase is a ligase that can ligate a 5' DNA end adjacent to a 3' DNA end of the one or more linear DNA fragments bridged by the endogenous circular RNA molecule scaffold.

3. The method of claim 1, wherein the ligase is selected from the group consisting of T4 DNA ligase, T4 RNA ligase, and *Paramecium bursaria Chlorella* virus 1 (PBCV-1) DNA Ligase.

4. The method of claim 1, wherein the ligase is PBCV-1 DNA Ligase.

5. The method of claim 1, further comprising prior to ligation, extending with a reverse transcriptase one or more DNA primers annealed to the endogenous circular RNA molecule scaffold to form the one or more linear DNA fragments bound to the endogenous circular RNA molecule scaffold.

6. The method of claim 5, wherein the reverse transcriptase is a recombinant of M-MLV reverse transcriptase from Moloney murine leukemia virus, HIV-1 reverse transcriptase from human immunodeficiency virus type 1, or AMV reverse transcriptase from avian myeloblastosis virus, and wherein said recombinant exhibits reduced RNase H activity and increased thermostability.

7. The method of claim 5, further comprising prior to extending the one or more DNA primers, priming the endogenous circular RNA molecule scaffold with the one or more DNA primers.

8. The method of claim 7, wherein the endogenous circular RNA molecule is primed by random priming using one or more random DNA primers and the one or more random DNA primers is from 6 to 8 bases in length.

9. The method of claim 7, wherein the endogenous circular RNA molecule is primed by non-random priming using one or more non-random DNA primers and the one or more non-random DNA primers is at least 8 bases in length.

10. The method of claim 1, further comprising prior to ligation, incubating the endogenous circRNA-DNA heteroduplex with a nuclease that targets single-stranded DNA to digest displaced cDNA flaps of the one or more linear cDNA fragments.

11. The method of claim 10, wherein the nuclease is selected from the group consisting of T5 Exonuclease, Mung Bean Nuclease (MBN), *Aspergillus* nuclease S1 (S1 Nuclease), Exonuclease VII (Exo VII), and *Escherichia coli* exonuclease V (RecBCD).

12. The method of claim 10, wherein the nuclease is T5 Exonuclease.

13. The method of claim 1, wherein following ligation of the one or more linear cDNA fragments bound to the endogenous circular RNA molecule scaffold, the endogenous circRNA-DNA heteroduplex comprising the endogenous circular RNA molecule scaffold and the covalently closed circular cDNA molecule is formed, and wherein the method further comprises digesting the RNA portion of the endogenous circRNA-DNA heteroduplex comprising the endogenous circular RNA molecule scaffold and the covalently closed circular cDNA molecule with an RNase.

14. The method of claim 13, wherein the RNase is RNase H.

15. The method of claim 1, wherein following ligation of the one or more linear cDNA fragments bound to the endogenous circular RNA molecule scaffold to construct the covalently closed circular cDNA molecule, incubating a sample comprising the covalently closed circular cDNA molecule with an exonuclease to digest linear DNA.

16. The method of claim 15, wherein the exonuclease is selected from the group consisting of RecBCD (Exonuclease V), T5 exonuclease, RecJ, Exonuclease T, and Exonuclease VII (Exo VII).

* * * * *